United States Patent [19]

Garrison et al.

[11] Patent Number: 5,613,937
[45] Date of Patent: Mar. 25, 1997

[54] METHOD OF RETRACTING HEART TISSUE IN CLOSED-CHEST HEART SURGERY USING ENDO-SCOPIC RETRACTION

[75] Inventors: Michi E. Garrison, Belmont; Sean C. Daniel, San Francisco, both of Calif.

[73] Assignee: Heartport, Inc., Redwood City, Calif.

[21] Appl. No.: 294,454

[22] Filed: Aug. 23, 1994

Related U.S. Application Data

[63] Continuation-in-part of Ser. No. 163,241, Dec. 6, 1993, Pat. No. 5,571,215, which is a continuation-in-part of Ser. No. 23,778, Feb. 22, 1993, Pat. No. 5,452,733.

[51] Int. Cl.[6] ........................................ A61B 1/22
[52] U.S. Cl. .................... 600/201; 600/208; 600/215; 128/898
[58] Field of Search ................................. 600/201, 204, 600/208, 213, 215, 219, 226; 128/898; 604/49, 142; 606/46; 623/2

[56] References Cited

U.S. PATENT DOCUMENTS

| | | |
|---|---|---|
| 4,122,844 | 10/1978 | Rabban . |
| 5,127,393 | 7/1992 | McFarlin et al. . |
| 5,167,223 | 12/1992 | Koros et al. ............................ 128/20 |
| 5,174,278 | 12/1992 | Babkow . |
| 5,231,974 | 8/1993 | Giglio et al. . |
| 5,304,183 | 4/1994 | Gourlay et al. . |
| 5,392,156 | 2/1995 | Hildwein et al. ........................ 604/174 |
| 5,441,042 | 8/1995 | Putman . |
| 5,441,059 | 8/1995 | Dannan . |
| 5,452,733 | 9/1995 | Sterman et al. ........................ 128/898 |

FOREIGN PATENT DOCUMENTS

| | | |
|---|---|---|
| WO93/09720 | 5/1993 | WIPO . |
| WO93/09709 | 5/1993 | WIPO . |

OTHER PUBLICATIONS

Scanlan International, Inc., Surgical Instrumentation Catalog, 1992, p. 81.
Pilling Co., Surgical Instruments Catalog, 1993, pp. 294–296.
Carter, M. G. "A New Retractor for Open Mitral Valve Surgery," (1962) *Journal of Thoracic and Cardiovascular Surgery*, vol. 44, No. 2.

*Primary Examiner*—Richard J. Apley
*Assistant Examiner*—Beverly M. Flanagan
*Attorney, Agent, or Firm*—Townsend and Townsend and Crew LLP

[57] ABSTRACT

The invention provides a system and method for manipulating a tissue structure within a body cavity. In a preferred embodiment, the invention provides a system and method for retracting and supporting the heart wall to provide access into the heart during a cardiac surgical procedure. The system comprises a tissue supporting member (500) positionable through a first percutaneous intercostal penetration into the thoracic cavity. The tissue supporting member has a contact surface (502) configured for supporting a portion of the heart wall. A retractor (40a) includes a shaft (400) with a proximal end, a distal end configured for introduction through a second percutaneous penetration and a diameter less than the width and length of the contact surface. A hook (428) is slidably coupled to the distal end of the shaft for releasably holding the tissue supporting member such that the contact surface is arranged transversely to the longitudinal axis of the shaft. With this configuration, the shaft and tissue supporting member can be introduced through two separate percutaneous penetrations and connected together within the thoracic cavity for retraction of the heart wall.

21 Claims, 29 Drawing Sheets

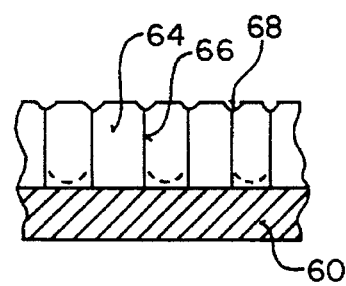
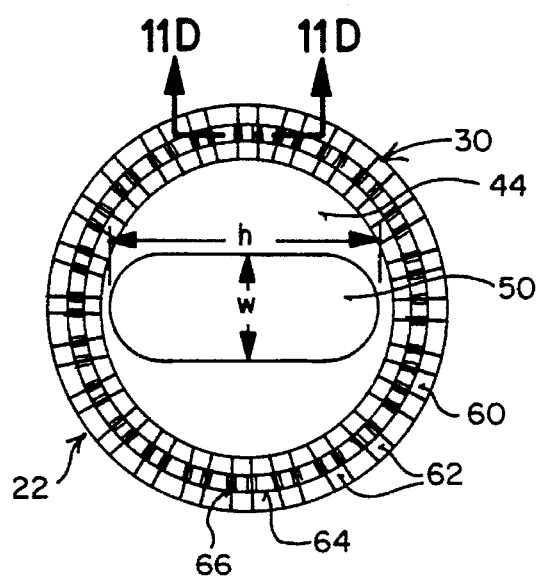
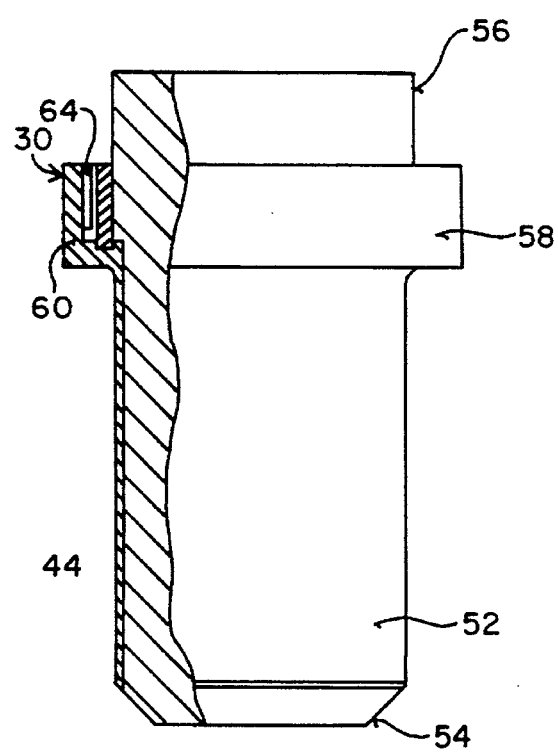
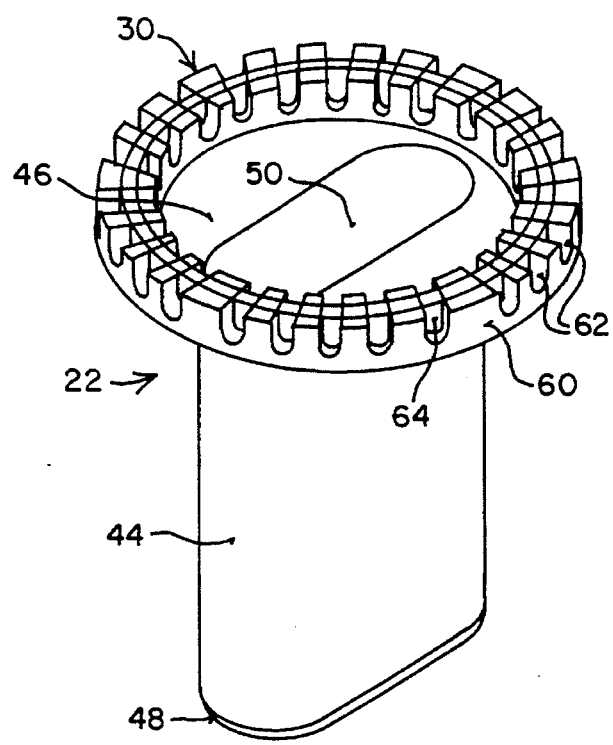

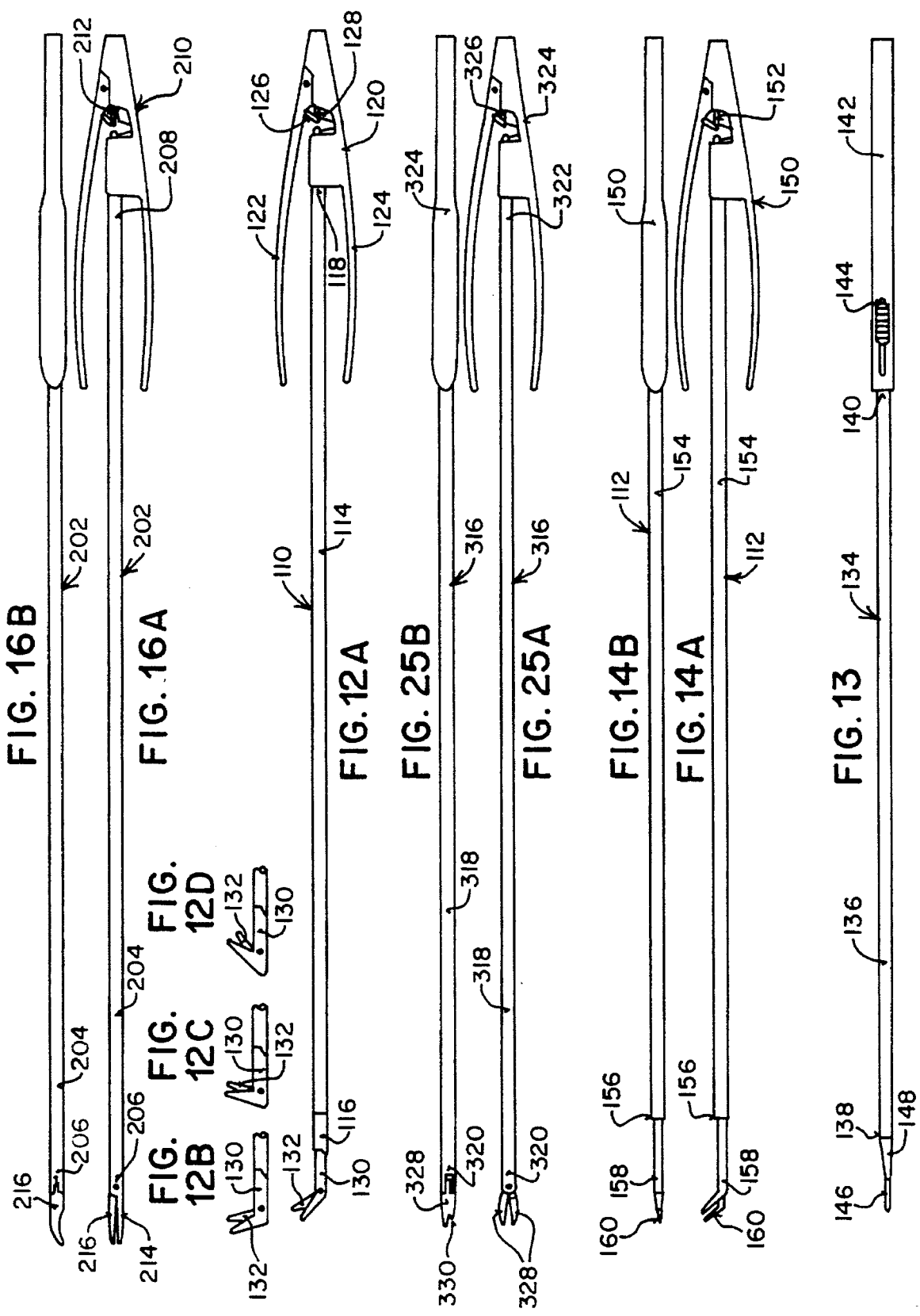

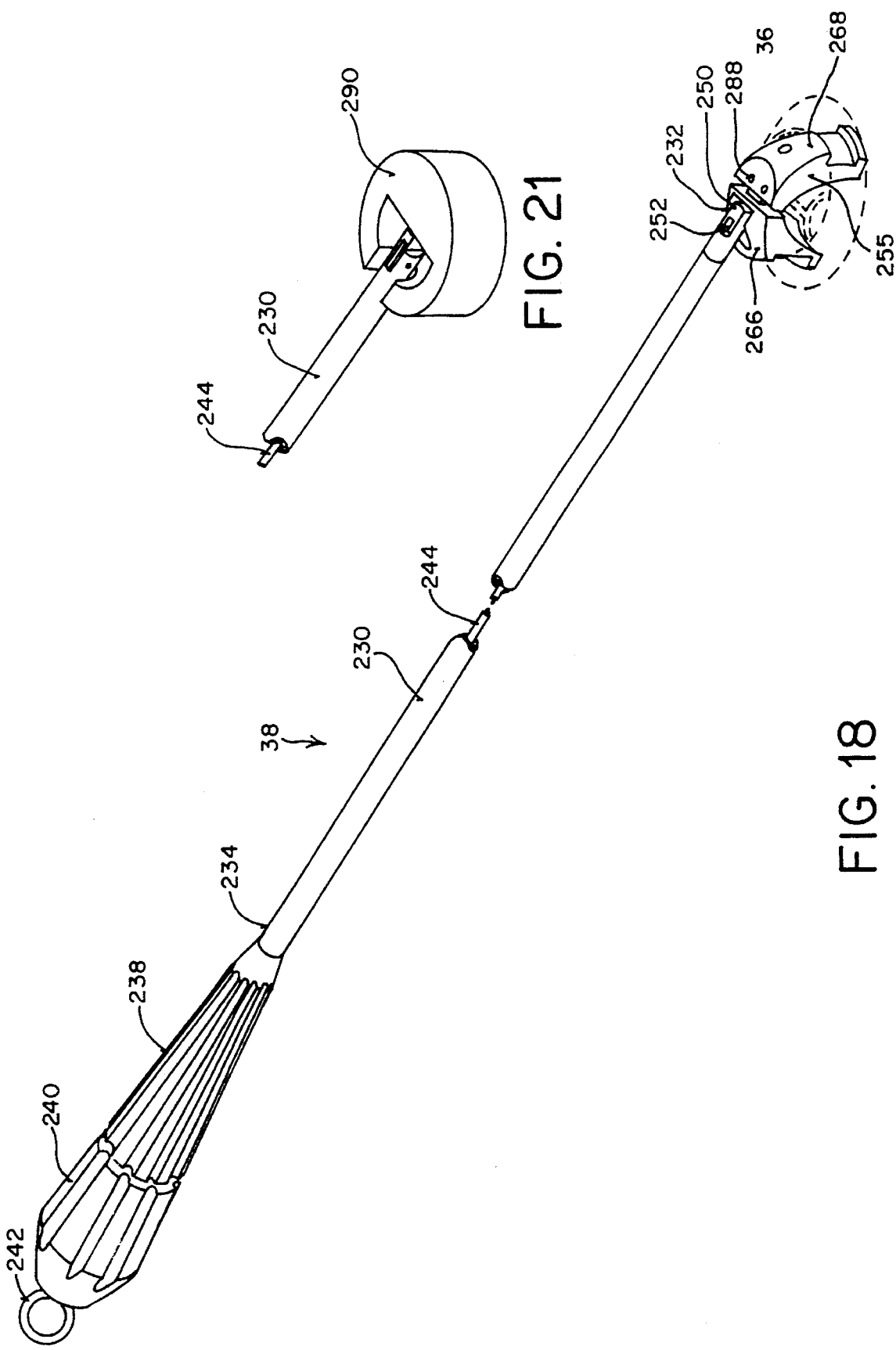

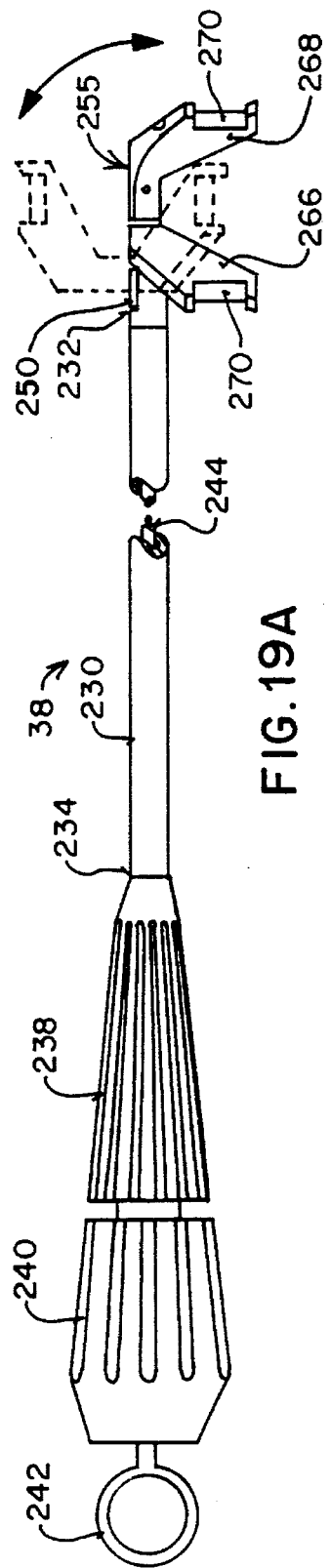
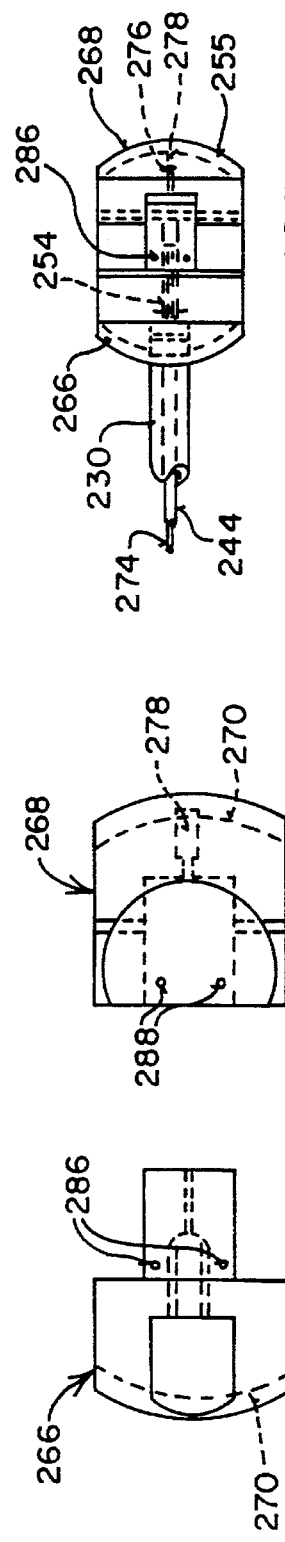
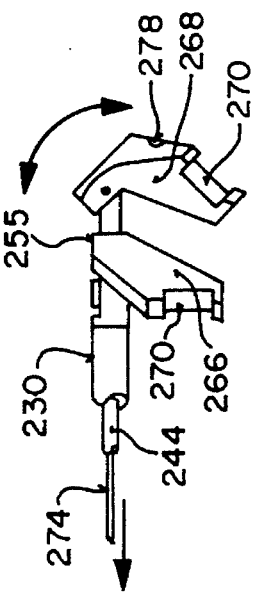
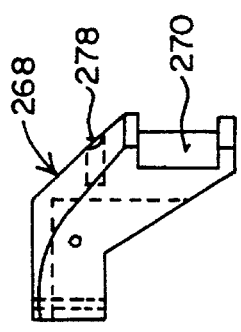
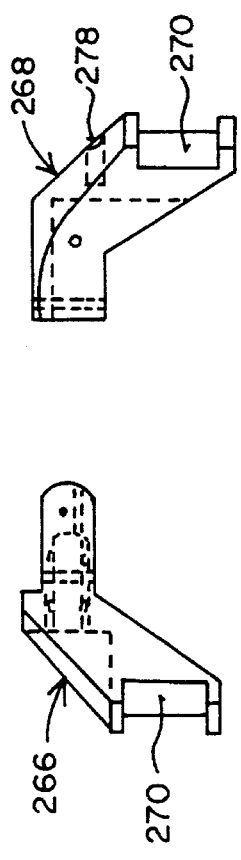

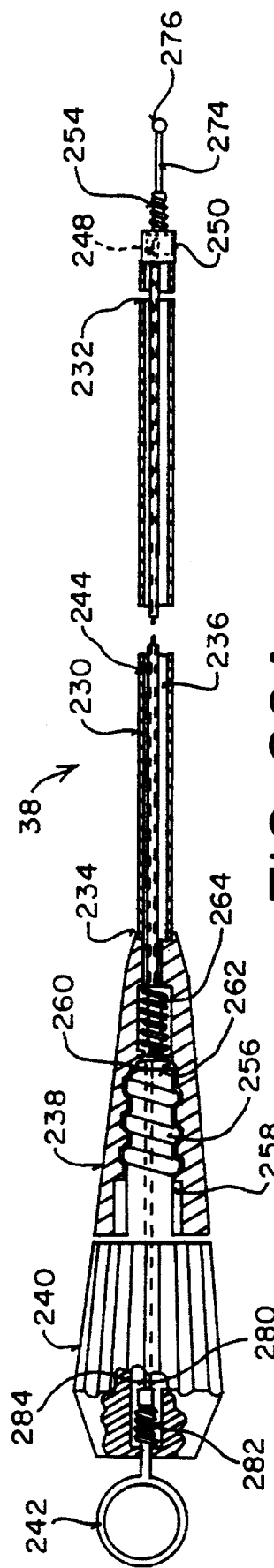
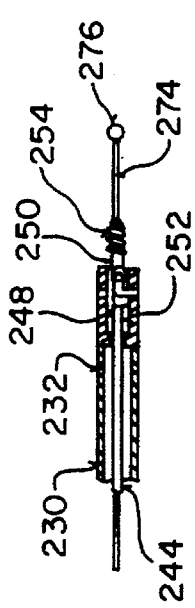
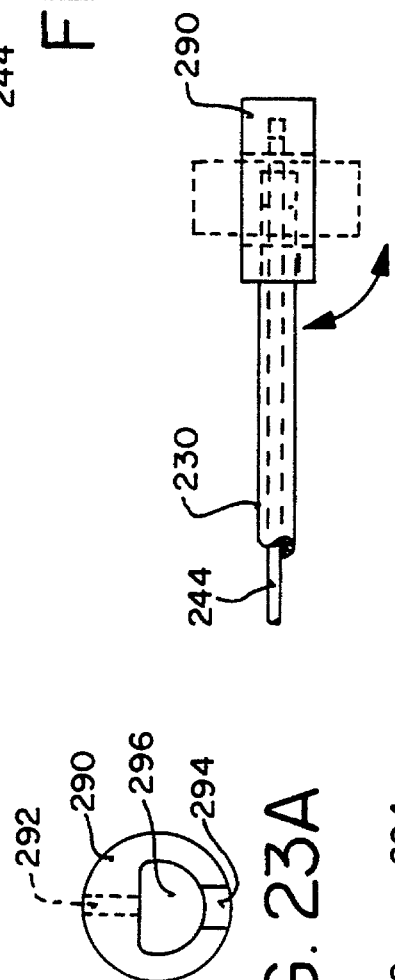
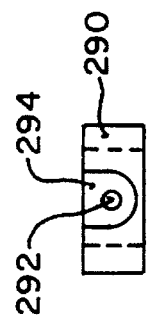
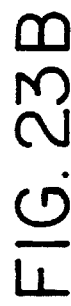

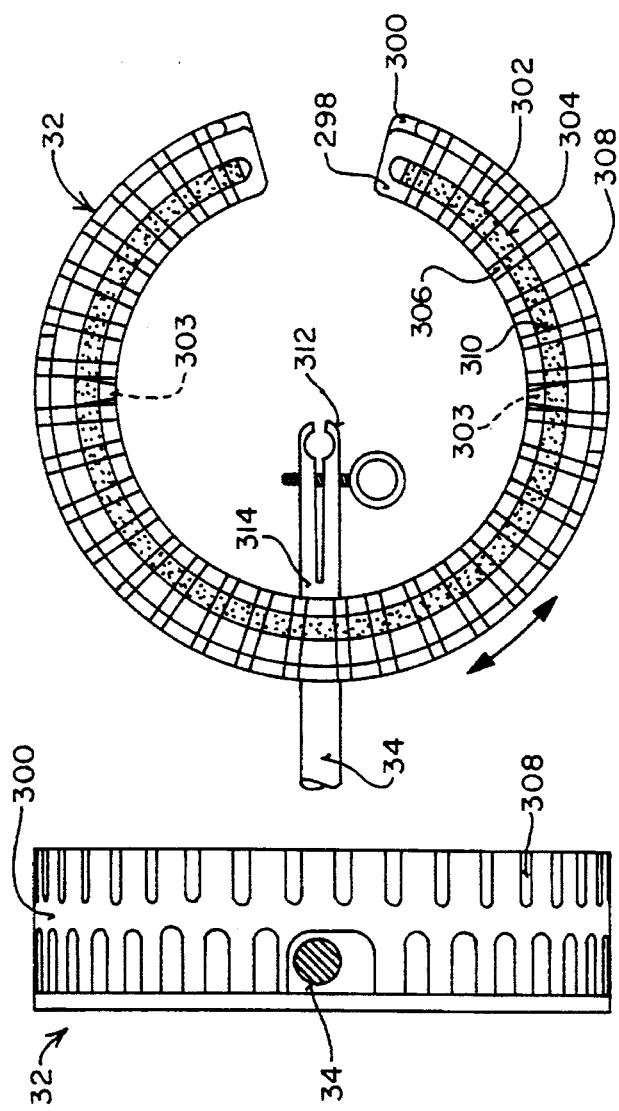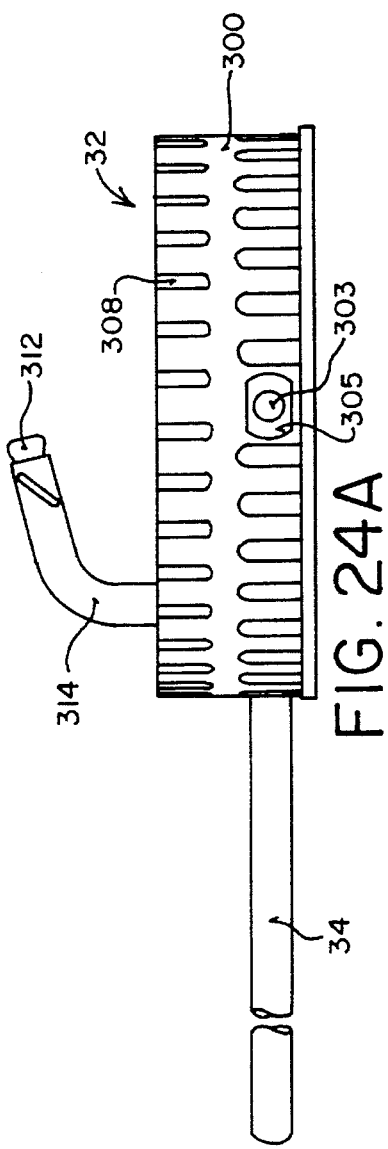

METHOD OF RETRACTING HEART TISSUE IN CLOSED-CHEST HEART SURGERY USING ENDO-SCOPIC RETRACTION

CROSS-REFERENCE TO RELATED APPLICATIONS

This application is a continuation-in-part of commonly-assigned, application Ser. No. 08/163,241, filed Dec. 6, 1993, now U.S. Pat. No. 5,571,215 which is a continuation-in-part of application Ser. No. 08/023,778, filed Feb. 22, 1993, now U.S. Pat. No. 5,452,733. The complete disclosures of these applications are hereby incorporated herein by reference.

FIELD OF THE INVENTION

This invention relates generally to instruments and techniques for performing less-invasive surgical procedures, and more specifically, to less-invasive instruments and techniques for retracting tissue structures within body cavities such as the abdomen or thorax.

BACKGROUND OF THE INVENTION

Various types of surgical procedures are currently performed to investigate, diagnose, and treat diseases of the heart and the great vessels of the thorax. Such procedures include repair and replacement of mitral, aortic, and other heart valves, repair of atrial and ventricular septal defects, pulmonary thrombectomy, treatment of aneurysms, electrophysiological mapping and ablation of the myocardium, and other procedures in which interventional devices are introduced into the interior of the heart or a great vessel.

Using current techniques, many of these procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents.

Surgical intervention within the heart generally requires isolation of the heart and coronary blood vessels from the remainder of the arterial system, and arrest of cardiac function. Usually, the heart is isolated from the arterial system by introducing an external aortic crossclamp through a sternotomy and applying it to the aorta between the brachiocephalic artery and the coronary ostia. Cardioplegic fluid is then injected into the coronary arteries, either directly into the coronary ostia or through a puncture in the aortic root, so as to arrest cardiac function. In some cases, cardioplegic fluid is injected into the coronary sinus for retrograde perfusion of the myocardium. The patient is placed on cardiopulmonary bypass to maintain peripheral circulation of oxygenated blood.

Of particular interest to the present invention are intracardiac procedures for surgical treatment of heart valves, especially the mitral and aortic valves. According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of valve and annulus tissue. Alternatively, the valve may be replaced, by excising the valve leaflets of the natural valve, and securing a replacement valve in the valve position, usually by suturing the replacement valve to the natural valve annulus. Various types of replacement valves are in current use, including mechanical and biological prostheses, homografts, and allografts, as described in Bodnar and Frater, *Replacement Cardiac Valves* 1–357 (1991), which is incorporated herein by reference. A comprehensive discussion of heart valve diseases and the surgical treatment thereof is found in Kirklin and Barratt-Boyes, *Cardiac Surgery* 323–459 (1986), the complete disclosure of which is incorporated herein by reference.

The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into an anterior position accessible through the sternotomy. An opening, or atriotomy, is then made in the right side of the left atrium, anterior to the right pulmonary veins. The atriotomy is retracted by means of sutures or retraction devices, exposing the mitral valve directly posterior to the atriotomy. One of the aforementioned techniques may then be used to repair or replace the valve.

An alternative technique for mitral valve access may be used when a median sternotomy and/or rotational manipulation of the heart are undesirable. In this technique, a large incision is made in the right lateral side of the chest, usually in the region of the fourth intercostal space. One or more ribs may be removed from the patient, and other ribs near the incision are retracted outward to create a large opening into the thoracic cavity. The left atrium is then exposed on the posterior side of the heart, and an atriotomy is formed in the wall of the left atrium, through which the mitral valve may be accessed for repair or replacement.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of a replacement valve through the atriotomy for attachment within the heart. However, these invasive, open-chest procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

In response to the various problems associated with open-chest procedures, new methods of performing closed-chest surgery on the heart using minimally invasive thoracoscopic techniques have been recently developed. In these methods, the patient's heart is arrested by occluding the patient's aorta between the coronary arteries and the brachiocephalic artery with an expandable balloon on the distal end of an endovascular catheter introduced via a femoral artery. Cardioplegic fluid is then delivered to the patient's myocardium through a lumen in the same catheter or through a catheter positioned in the coronary sinus via a peripheral vein. To repair or replace the mitral valve, minimally-invasive cutting and suturing instruments are then introduced thoracoscopically through a trocar sleeve in the right lateral portion of the chest. A complete description of such methods is found in commonly assigned, co-pending application Ser. No. 08/163,241, filed Dec. 6, 1993, which is incorporated herein by reference.

This new generation of thoracoscopic methods of performing heart valve repair has, of course, created many new challenges. One such challenge is that of retracting the left atrial wall to open the atriotomy so that the mitral valve can be exposed for the surgical procedure. The heart wall must be retracted anteriorly to suitably expose the mitral valve and provide access through the atriotomy for the cutting and suturing instruments introduced through the right lateral portion of the chest. In addition, the instruments that retract the heart wall must be introduced in a minimally-invasive manner through small percutaneous incisions or cannulae positioned in intercostal spaces in the patient's rib cage.

Introducing an instrument through an intercostal space in the anterior side of the chest presents additional problems. One such problem is that the patient's rib cage is typically structured so that the ribs in the anterior portion of the chest are closer together than in the lateral portions of the chest. In addition, the tissue layer in the anterior chest wall contains nerves that could be damaged by a large percutaneous incision. Therefore, a retraction device introduced from the anterior side should be as small as possible, preferably on the order of 3–8 mm, to fit within the smaller anterior intercostal spaces and to avoid unnecessary trauma to the patient. Another problem is that the part of the retraction device that engages the heart wall must be wide enough to engage a sufficient portion of the heart wall to open the atriotomy enough to expose the mitral valve. It must also be long enough to extend a sufficient distance into the heart to extend beneath the interatrial septum and prevent it from sagging or otherwise inhibiting access to the mitral valve. Introducing an instrument which is large enough to sufficiently expose the mitral valve through the smaller intercostal spaces in the anterior portion of the chest is problematic.

What is needed, therefore, are improved systems and methods for manipulating a tissue structure in a body cavity via a small percutaneous incision or cannula. Preferably, the systems and methods would be capable of retracting an incision in a vessel or organ, such as an atriotomy in the left atrium to expose the mitral valve for repair or replacement. The system should be configured for introduction through an extremely small percutaneous penetration, such as a cannula positioned in an anterior intercosial space. The system should also be large enough to retract the heart wall sufficiently to expose the mitral valve and to support the interatrial septum. In addition, the system should be configured to facilitate retraction of the left atrium from the anterior side of the chest.

SUMMARY OF THE INVENTION

The invention provides systems and methods for manipulating a tissue structure in a body cavity through a small percutaneous penetration in a patient. The system is configured for being introduced through a small percutaneous penetration into a body cavity and retracting an incision in the left atrium from the anterior side of the chest. The system is well suited for engaging the heart wall, making the invention particularly useful during surgeries such as mitral valve replacement. The system is wide enough to retract a sufficient portion of the heart wall to expose the left atrium and long enough to extend into the heart and support the interatrial septum. While being especially useful for thoracoscopy, the system and method are also useful in other surgical procedures, such as laparoscopy and pelviscopy.

In one aspect of the invention, the system comprises a tissue supporting member positionable through a first percutaneous penetration into a body cavity. The tissue supporting member has a contact surface configured for supporting at least a portion of the tissue structure. A shaft has a proximal end, a distal end configured for introduction through a second percutaneous penetration and a diameter less than the width and length of the contact surface. A connection means is coupled to the distal end of the shaft for releasably holding the tissue supporting member such that the contact surface is arranged transversely to the longitudinal axis of the shaft. With this configuration, the shaft and tissue supporting member can be introduced through two separate percutaneous penetrations and connected together within a body cavity. This allows the shaft to be introduced through a small intercosial space in the anterior side of the chest from the direction in which retraction will occur, while the tissue supporting member is introduced through a larger intercosial space in the lateral side of the chest.

In one embodiment, the tissue supporting member includes a support plate having an arcuate upper surface configured for supporting the tissue structure. Preferably, the arcuate upper surface has a curvature selected to conform to an opening in the tissue structure. The upper surface is long enough to extend relatively deep beneath the tissue structure to support a relatively thick outer wall of a vessel or organ. The upper surface is also wide enough to allow the surgeon to substantially enlarge the opening so that an inner cavity of the tissue structure is exposed. The support plate may also include means for retaining the tissue wall on the contact surface. Preferably, the retaining means comprises a lip that projects upwards from the upper surface on at least one end of the tissue supporting member. The lip prevents the tissue wall from sliding along the upper surface and off of the support plate. The upper surface may also include grooves for frictionally engaging the tissue wall.

In a second embodiment, the tissue supporting member includes a pair of arms extending transversely from the distal end of the shaft. The arms are disposed apart from each other and preferably form a "V" shape to allow the surgeon to retract a substantial portion of the tissue wall. Each arm has an upper surface configured to extend relatively deep beneath the tissue structure to engage the outer tissue wall. The arms may further include distal tips that curve upwards to prevent the tissue wall from sliding off the upper surfaces.

In a third embodiment, the tissue supporting member includes an expandable member coupled to the distal end of the shaft. Preferably, the expandable member is a balloon that is movable into an expanded configuration for supporting the tissue structure. In the expanded configuration, the balloon is large enough to substantially enlarge the opening in the tissue structure and to extend beneath the tissue structure to support the outer wall. To expand the balloon, the shaft further includes a lumen fluidly coupling the balloon with an inflation means at the proximal end of the shaft.

In a preferred embodiment, the connections means includes a hook slidably coupled to the distal end of the shaft. The tissue supporting member has an opening configured for receiving the hook so that the shaft holds the tissue supporting member with the contact surface arranged transversely to the longitudinal axis of the shaft. Preferably, the contact surface is disposed at an angle of at most 110°, usually less than 90°, relative to the longitudinal axis of the shaft so that it can easily support the tissue wall. The connection means rigidly holds the contact surface so that the contact surface will be maintained at this angle relative to the shaft. In this manner, the surgeon may apply a force to the shaft to manipulate the tissue structure with the contact surface.

In one embodiment, the hook includes a U-shaped distal tip to ensure that the hook remains engaged with the opening in the tissue supporting member. In a second embodiment, the hook includes an L-shaped distal tip to facilitate the surgeon's engagement of the tip with the opening.

The invention may further include actuator means at the proximal end of the shaft for moving the shaft with respect to the hook between a first position, where the tissue supporting member is locked to the shaft, and a second position, where the tissue supporting member is releasable from the shaft. Preferably, the shaft is biased into the second position by biasing means such as a spring. The actuator means may further include a locking mechanism to maintain the shaft in the first position and means to release the locking mechanism so that the biasing means can move the shaft into the second position.

In a preferred embodiment, the invention includes a clamping means for fixing the shaft in a longitudinal position with respect to the second percutaneous penetration. The clamping means may include a collar slidably coupled to the shaft and means such as a set screw or clamping ring for locking the collar at a particular longitudinal position along the shaft. The collar is configured to rest against an outer surface of the patient's body or a proximal end of a trocar sleeve so that the shaft will not move in the distal direction. In this manner, the surgeon can exert traction on the shaft to manipulate the tissue structure into a desired position and then fix the shaft so that the tissue structure will remain in a stationary position without being held by the surgeon.

The invention may further include an introducer for introducing the tissue supporting member into the body cavity. The introducer includes a second shaft with proximal and distal ends and a longitudinal axis therebetween. The distal end is preferably configured for introduction through an intercostal space. The introducer includes means at the distal end for releasably holding the tissue supporting member. Preferably, the holding means holds the tissue supporting member such that the contact surface is generally parallel to the longitudinal axis of the second shaft. This minimizes the cross-sectional profile of the tissue supporting member and the introducer to facilitate delivery of the tissue supporting member through the intercostal space. In addition, the tissue supporting member is suitably positioned for connection to the first shaft within the body cavity.

In a preferred embodiment, the holding means of the introducer is a hook slidably coupled to the distal end of the shaft such that the shaft can move relative to the hook. The tissue supporting member has a second opening configured for receiving the hook. Preferably, the opening is disposed on an opposite end from the first opening such that the first shaft and the introducer can simultaneously hold the tissue supporting member. In this configuration, the introducer will be generally perpendicular to the first shaft, allowing the introducer to be positioned in a lateral side of the chest while the first shaft is positioned in the anterior side of the chest. The tissue supporting member may further include a third opening disposed proximate to the first opening so that the first shaft and the introducer can engage the tissue supporting member on the same side, if desired.

The invention is particularly useful for retracting and supporting the walls of the heart during a cardiac procedure such as repairing or replacing the mitral valve. In this procedure, the patient's heart is placed under cardioplegic arrest and the patient is supported on cardiopulmonary bypass. A first access cannula is positioned in a first percutaneous intercostal penetration in the right lateral side of the patient's chest and a second access cannula is positioned in a second, much smaller percutaneous intercostal penetration in the anterior side of the patient's chest. A viewing scope is introduced through another right anterior percutaneous intercostal penetration. A cutting tool is introduced through the first access cannula in the right lateral chest to form an incision or atriotomy in the wall of the left atrium.

To enlarge the atriotomy in the left atrium and expose the mitral valve in a line of sight from the first access cannula in the right chest, the first shaft is introduced through the second access cannula. The tissue supporting member, releasably connected to the introducer, is then guided through the first access cannula and positioned within the thoracic cavity adjacent the first shaft. The first shaft is manipulated to engage the first opening of the tissue supporting member with the hook, and the first shaft is moved in the distal direction with respect to the hook so that the tissue supporting member is locked to the first shaft with the contact surface arranged transversely to the longitudinal axis of the first shaft.

Once the tissue supporting member has been connected to the first shaft, the introducer is disengaged from the tissue supporting member and withdrawn from the patient. The tissue supporting member is then positioned in the atriotomy such that the heart wall is adjacent to the contact surface. To enlarge the atriotomy, the surgeon moves the shaft and the hook in the proximal direction to pull upwards on the tissue supporting member thereby retracting the heart wall anteriorly. The tissue supporting member sufficiently enlarges the atriotomy to expose the mitral valve and supports the interatrial septum so that it does not inhibit access to the mitral valve. The surgeon then moves the collar into the locked position around the shaft to prevent the shaft from moving in the distal direction. This ensures that the heart wall will remain retracted during the operation.

After the heart wall has been retracted to expose the mitral valve, a cutting tool may be introduced through the first access cannula to remove all or part of the mitral valve. A replacement valve can then be introduced through the first access cannula and fastened within the heart, usually by suturing the replacement valve to an annulus at the natural valve position in the heart. Once the mitral valve has been replaced, the collar is moved into the open position to release the first shaft, allowing the first shaft to move distally to close the atriotomy. The tissue supporting member is removed from the atriotomy, and the introducer is reintroduced through the first access cannula to engage the tissue supporting member. The tissue supporting member is then released from the first shaft by moving the first shaft in a proximal direction relative to the hook The introducer and the tissue supporting member may then be withdrawn from the patient through the access cannula.

In a preferred embodiment, the shaft has an outer diameter less than about 5 mm allowing the second intercostal penetration to be of the same or slightly larger size, e.g. less than about 8 mm. This reduces the trauma to the patient and avoids the possibility of damaging nerves in the patient's chest. In addition, the small diameter shaft facilitates penetrating the tighter intercostal spaces in the anterior side of the chest.

In an exemplary embodiment, the contact surface has a width and a length each greater than about 20 mm. The relatively large dimensions of the contact surface allow the surgeon to retract a substantial portion of the heart wall to suitably expose the mitral valve for an approach from the right side of the chest. In addition, the surgeon can insert the contact surface deeply enough into the left atrium to support the interatrial septum so that it does not sag or otherwise inhibit access to the mitral valve.

It should be understood that while the invention is described in the context of thoracoscopic surgery on the left atrium and mitral valve, the systems and methods disclosed herein are equally useful on other types of tissue structures and in other types of surgery, such as laparoscopy and pelviscopy.

A further understanding of the nature and advantages of the invention may be realized by reference to the remaining portions of the specification and the drawings. dr

BRIEF DESCRIPTION OF THE DRAWINGS

FIGS. 11A–11C are perspective, front, and top views respectively of the access cannula in the system of FIG. 1;

FIG. 11D is a partial cut-away view taken along line 11D—11D in FIG. 11C;

FIG. 12A is a side view of angled scissors in the system of FIG. 1;

FIGS. 12B–12D are side views of a distal portion of the scissors of FIG. 12A showing alternative embodiments thereof;

FIG. 13 is a side view of a retractable knife in the system of FIG. 1;

FIGS. 14A–14B are side and top views, respectively, of grasping forceps in the system of FIG. 1;

FIGS. 16A–16B are side and top views, respectively, of needle drivers in the system of FIG. 1.

FIG. 18 is a perspective view of a prosthesis introducer in the system of FIG. 1;

FIG. 19A is a side view of the prosthesis introducer of FIG. 18;

FIGS. 19B–19C are bottom and side views, respectively, of a distal portion of the prosthesis introducer of FIG. 18;

FIGS. 19D–19E are top and side views, respectively, of a stationary arm of the prosthesis introducer of FIG. 18;

FIGS. 19F–19G are top and side views, respectively, of a movable arm of the prosthesis introducer of FIG. 18;

FIG. 20A is a side partial cut-away view of the prosthesis introducer of FIG. 18;

FIG. 20B is a top partial cut-away view of a distal portion of the prosthesis introducer of FIG. 18;

FIG. 21 is a perspective view of a sizing disk in the system of FIG. 1, positioned on the introducer of FIG. 18;

FIGS. 22, 23A and 23B are top and side views, respectively, of the sizing disk of FIG. 21;

FIGS. 24A–24C are front, top, and side views, respectively of a suture organizing ring in the system of FIG. 1;

FIGS. 25A–25B are side and top views, respectively of a knot-pushing device in the system of FIG. 1;

DETAILED DESCRIPTION OF SPECIFIC EMBODIMENTS

The invention provides methods and devices for performing surgical interventions within the heart or a great vessel such as the aorta, superior vena cava, inferior vena cava, pulmonary artery, pulmonary vein, coronary arteries, and coronary veins, among other vessels. While the specific embodiments of the invention described herein will refer to mitral valve repair and replacement, it should be understood that the invention will be useful in performing a great variety of surgical procedures, including repair and replacement of aortic, tricuspid, or pulmonary valves, repair of atrial and ventricular septal defects, pulmonary thrombectomy, removal of atrial myxoma, patent foramen ovale closure, treatment of aneurysms, electrophysiological mapping and ablation of the myocardium, myocardial drilling, coronary artery bypass grafting, angioplasty, atherectomy, correction of congenital defects, and other procedures in which interventional devices are introduced into the interior of the heart, coronary arteries, or great vessels. Advantageously, the invention facilitates the performance of such procedures through percutaneous penetrations within intercostal spaces of the rib cage, obviating the need for a median sternotomy or other form of gross thoracotomy.

The terms "percutaneous intercostal penetration" and "intercostal penetration" as used herein refer to a penetration, in the form or a small cut, incision, hole, cannula, trocar sleeve, or the like, through the chest wall between two adjacent ribs, wherein the patient's rib cage and sternum remain substantially intact, without cutting, removing, or significantly displacing the ribs or sternum. These terms are intended to distinguish a gross thoracotomy such as a median sternotomy, wherein the sternum and/or one or more ribs are cut or removed from the rib cage, or one or more ribs are retracted significantly, to create a large opening into the thoracic cavity. A "percutaneous intercostal penetration" may abut or overlap the adjacent ribs between which it is formed, but the maximum width of the penetration which is available for introduction of instruments, prostheses and the like into the thoracic cavity will be the width of the intercostal space, bounded by two adjacent ribs in their natural, substantially undeflected positions. It should be understood that one or more ribs may be retracted or deflected a small amount without departing from the scope of the invention; however, the invention specifically seeks to avoid the pain, trauma, and complications which result from the large deflection or cutting of the ribs in conventional, open-chest techniques.

Figure 1:
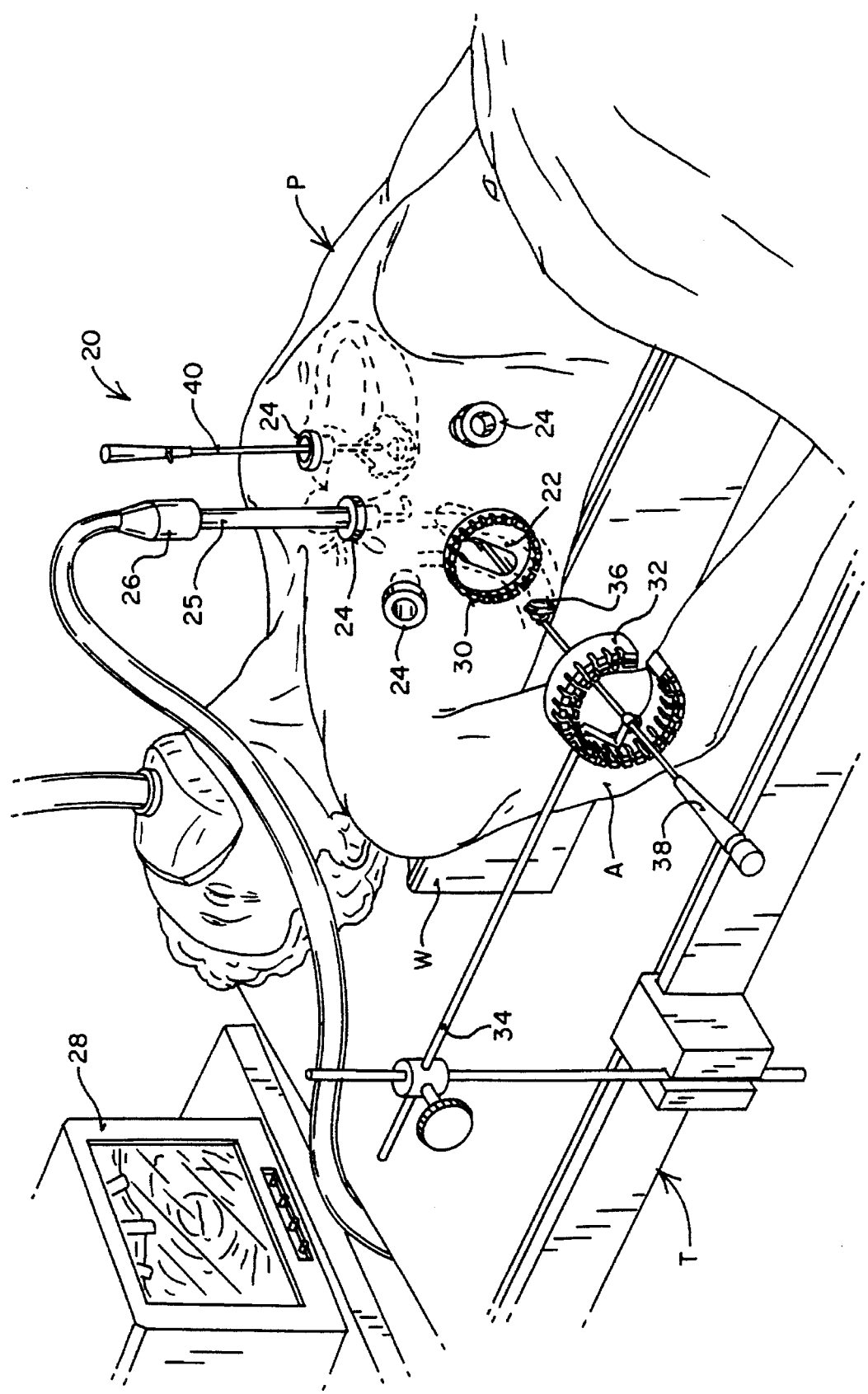
FIG. 1 is a perspective view of a system for closed-chest mitral valve replacement constructed in accordance with the principles of the present invention, showing the use of the system in a patient.

A first preferred embodiment of a system and method of closed-chest mitral valve replacement according to the invention will be described with reference to FIGS. 1–10. FIG. 1 illustrates a system 20 for closed-chest valve replacement positioned in a patient P on an operating table T. Preferably, a wedge or block W having a top surface angled at approximately 20° to 45° is positioned under the right side of patient P so that the right side of the patient's body is somewhat higher than the left side. The patient's right arm A is allowed to rotate downward to rest on table T, exposing the right lateral side of the patient's chest.

The valve replacement system 20 includes an access cannula 22 positioned percutaneously within an intercostal space between two ribs (shown in phantom) in a right lateral side of the patient's chest. Additional thoracoscopic trocar sleeves 24 of conventional construction are positioned within intercostal spaces in the right lateral chest inferior and superior to access cannula 22, as well as in the right anterior (or ventral) portion of the chest. An endoscope 25 of conventional construction is positioned through a percutaneous intercostal penetration into the patient's chest, usually through one of trocar sleeves 24. The distal end of endoscope 25 (shown in phantom) is preferably configured to view at an angle between about 30° and 90° relative to the shaft of endoscope 25, to facilitate visualization of the heart from the right portion of the thoracic cavity. A light source (not shown) is also provided on endoscope 25 to illuminate the thoracic cavity. A video camera 26 is mounted to the proximal end of endoscope 25, and is connected to a video monitor 28 for viewing the interior of the thoracic cavity. A first suture organizing ring 30 is mounted to a proximal end of access cannula 22. A second organizing ring 32 is mounted to a support stand 34 fixed to table T. A replacement valve 36 is held at the distal end of an introducer 38 between first organizing ring 30 and second organizing ring 32. Introducer 38 extends through second organizing ring 32 and is supported by support stand 34. Additional instruments to be used in a procedure such as a retractor 40, as well as cutting, suturing, stapling, aspirating, irrigating and other devices, may be introduced through access cannula 22, trocar sleeves 24, and/or small, percutaneous incisions within intercostal spaces of the rib cage.

Figure 2:
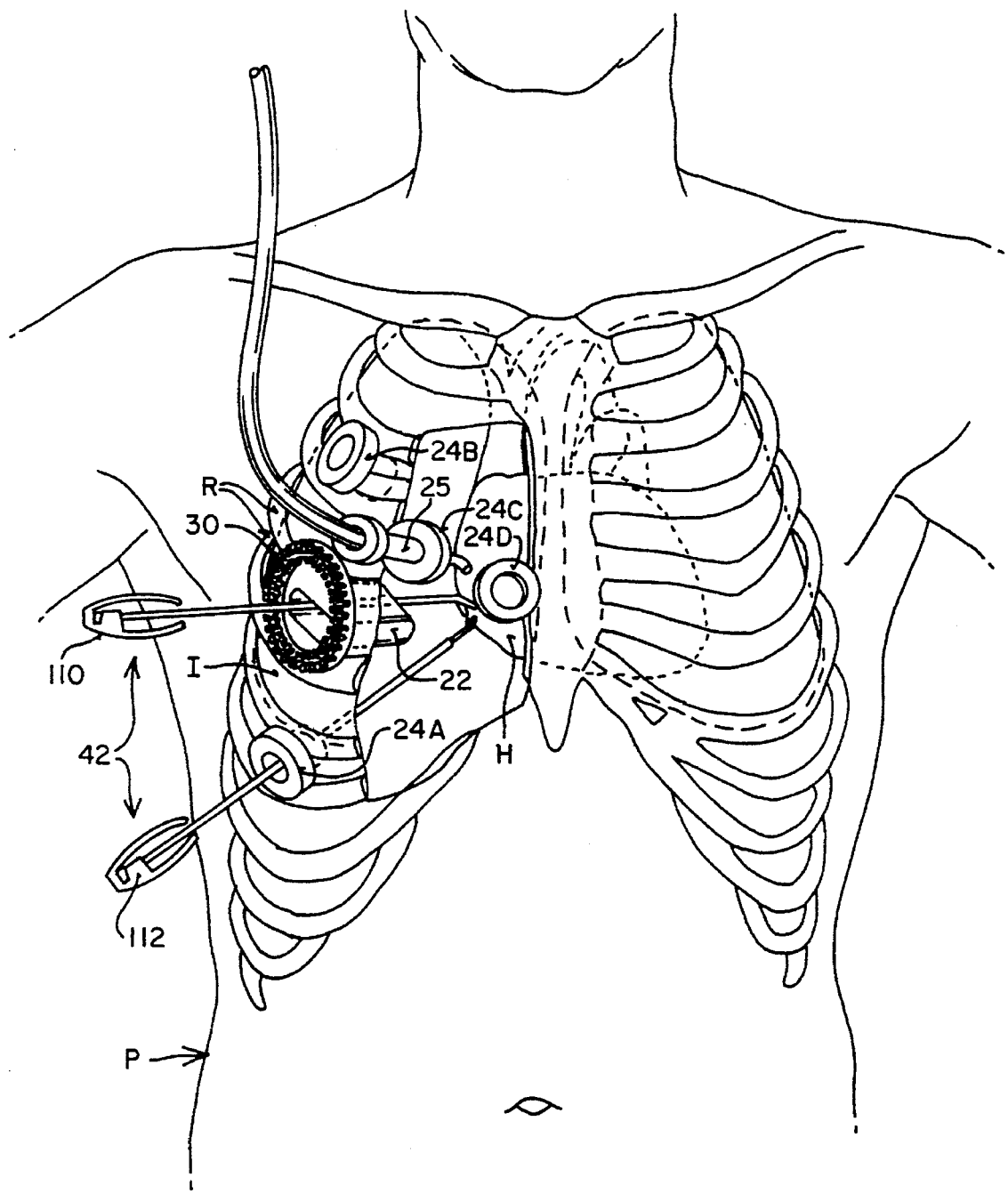
FIG. 2 is a front view of the system of FIG. 1, showing the positioning of the system in the patient's chest.

Referring now to FIG. 2, access cannula 22 is positioned within an intercostal space I in the right lateral side of the chest, preferably in the third, fourth, fifth, or sixth intercostal space between adjacent ribs R. Additional trocar sleeves 24A, 24B are positioned within intercostal spaces superior and inferior to access cannula 22 in the right lateral side of the chest. Access cannula 22 and trocar sleeves 24A, 24B are positioned so that instruments 42 introduced through them may be directed toward the right side of the left atrium of the heart H. A trocar sleeve 24C is positioned in an intercostal space in the right anterior side of the chest such that endoscope 25 may be introduced to view the thoracic cavity and heart H without interfering with instruments introduced through access cannula 22 or trocar sleeves 24A, 24B. An additional trocar sleeve 24D is positioned in an intercostal space in the anterior side of the chest just to the right of the sternum and anterior to the right lateral side of the heart H.

It will be understood to those of ordinary skill in the art that, in some cases, it may desirable to eliminate some or all of trocar sleeves 24 and/or access cannula 22, and introduce instruments directly through small, percutaneous intercostal incisions in the chest. Advantageously, unlike laparoscopic, arthroscopic, and other endoscopic procedures, no distension of the chest is required using the method of the invention, so that leakage of distension fluid through percutaneous penetrations is not of concern. Thus, either thoracoscopic trocar sleeves without fluid seals or percutaneous incisions may be utilized for instrument introduction into the thoracic cavity. Trocar sleeves are generally preferred, however, in order to provide an open passage into the thoracic cavity, to protect adjacent tissue from injury resulting from contact with instruments, and to avoid damaging instruments, endoscopes, replacement valves, and the like when introduced into the thoracic cavity.

Referring now to FIGS. 11A–11D, access cannula 22 will be described in greater detail. Access cannula 22 comprises a body 44 having a proximal end 46, a distal end 48, and a passage 50 extending therebetween. Body 44 is configured to fit within an intercostal space I without significant deflection of adjacent ribs R, usually having a width of less than about 20 mm. Passage 50 is configured to facilitate passage of replacement valve 36 therethrough. Replacement valve 36 may have a variety of configurations, but must have a diameter at least equal to that of the patient's natural heart valve, a diameter which commonly exceeds the width of the intercostal spaces in the rib cage. Therefore, in order to avoid cutting or retracting the patient's ribs, replacement valve 36 is introduced edge-first through passage 150 of access cannula 22, as described more fully below. To accommodate such introduction of replacement valve 36, passage 50 usually has a cross-sectional width w of about 12 mm to 20 mm, and a cross-sectional height h that is somewhat greater than cross-sectional width w, usually 2–6 times cross-sectional width w, and preferably in the range of 25 mm to 50 mm. Passage 50 may have various cross-sectional shapes, including oval, rectangular, race-track, and the like. This accommodates a variety of replacement heart valves, including mechanical and biological prostheses, as well as homograft and allograft tissue valves. It will be understood, however, that certain replacement valves may be collapsible or sufficiently small in size so that passage 50 in access cannula 22 may have a round or square cross-section and still allow passage of the replacement valve therethrough. However, a cross-sectional shape in which the height is greater than the width may still be advantageous to allow greater freedom of movement in manipulating the replacement valve and other instruments introduced through passage 150.

As shown in FIG. 11B, an obturator 52 is positionable in passage 150 to facilitate introduction of access cannula 22 through the chest wall. Obturator 52 has a tapered distal end 54, a proximal end 56, and a rim 58 near proximal end 56 for engaging proximal end 46 of cannula body 44. Usually, obturator 52 is positioned in passage 50 of access cannula 22, and the two are introduced through a small incision formed in an intercostal space in the chest wall. Obturator 52 is then removed from passage 50.

As described briefly above, access cannula 22 may further include a suture organizing ring 30 mounted to its proximal end 46. Suture organizing ring 30 has a ring-shaped body 60 and a plurality of slots 62 circumferentially spaced about body 60. Usually, between 16 and 32 of slots 62 are provided, depending upon the type of replacement valve and suturing technique to be utilized in the procedure. An elastomeric retaining ring 64 is disposed in a circumferential channel in ring body 60, and has a plurality of slits 66, best seen in FIG. 11D, aligned with each slot 62. Slits 66 are provided with chamfers 68 along the top surface of retaining ring 64 to facilitate positioning sutures within slits 66 for retention therein. The function of suture organizing ring 30 will be described in greater detail below.

Referring again to FIG. 2, once access cannula 22 and trocar sleeves 24 have been positioned in the patient's chest, endoscope 25 is introduced through trocar sleeve 24D and camera 26 is connected to video monitor 28 (FIG. 1). Endoscope 25 is manipulated so as to provide a view of the right side of the heart, and particularly, a right side view of the left atrium. Usually, an endoscope of the type having an articulated distal end, or a distal end disposed at an angle between 30° and 90° will be used, which is commercially available from, for example, Olympus Corp., Medical Instruments Division, Lake Success, N.Y.

As an alternative to the above viewing systems, a visualization system for direct, stereoscopic visualization of the thoracic cavity could be utilized, as described in commonly assigned, co-pending application Ser. No. 08/227,366, filed Apr. 13, 1994, which is a continuation-in-part of application Ser. No. 08/135,387, filed Oct. 8, 1993, since abandoned, which are incorporated herein by reference. This visualization system comprises a surgical microscope coupled to an access cannula. The access cannula can be positioned percutaneously in an intercostal space, facilitating direct stereoscopic visualization through the access cannula into the chest cavity. This system provides high image quality and the natural hand-eye coordination of direct vision while allowing multiple persons to simultaneously view the surgical site.

At this point in the procedure, if not previously accomplished, the patient is placed on cardiopulmonary bypass (CPB), the patient's right lung is at least partially collapsed, and the patient's heart is arrested. Suitable techniques for arresting cardiac function and establishing CPB without a thoracotomy are described in commonly-assigned, co-pending application Ser. No. 08/282,192, filed Jul. 28, 1994, which is a continuation-in-part of application Ser. No. 08/123,411, filed Sep. 17, 1993, since abandoned, and of application Ser. No. 08/310,818, filed Sep. 22, 1994, since abandoned, which is a continuation of application Ser. No. 07/991,188, filed Dec. 15, 1992, since abandoned, all of which are incorporated herein by reference.

Figure 3:
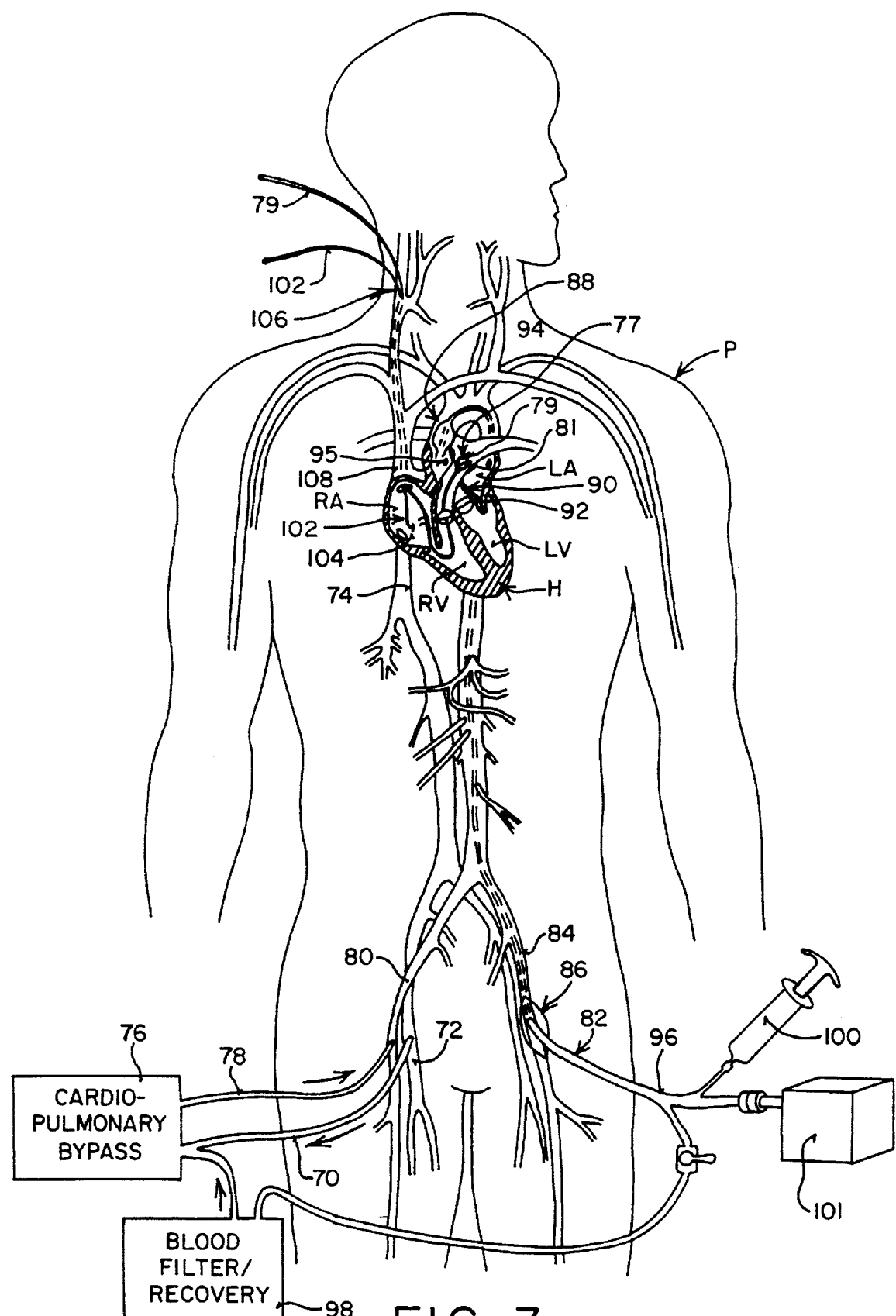
FIG. 3 is a front view of a patient's cardiovascular system illustrating the positioning of a system for arresting the heart and establishing cardiopulmonary bypass in accordance with the principles of the present invention.

As illustrated in FIG. 3, CPB is established by introducing a venous cannula 70 into a femoral vein 72 in patient P and advancing venous cannula 72 into the inferior vena cava 74 and/or into the interior of heart H to withdraw deoxygenated blood therefrom. Venous cannula 70 is connected to a cardiopulmonary bypass system 76 which receives the withdrawn blood, oxygenates the blood, and returns the oxygenated blood to an arterial return cannula 78 positioned in a femoral artery 80.

A pulmonary venting catheter 79 may also be utilized to withdraw blood from the pulmonary trunk 77. Pulmonary venting catheter 79 may be introduced from the neck through the interior jugular vein 106 and superior vena cava 108, or from the groin through femoral vein 72 and inferior vena cava 74. Usually, a Swan-Ganz catheter (not shown) is first introduced and positioned in pulmonary artery 77 using well-known techniques, and pulmonary venting catheter 79 is then introduced over the Swan-Ganz catheter. Blood is withdrawn from pulmonary trunk 77 through a port at the distal end of pulmonary venting catheter 79 and an inner lumen extending through the catheter outside of the patient's body. Pulmonary venting catheter 79 may further have one or more balloons 81 at its distal end proximal to the distal port for occluding pulmonary trunk 77.

An alternative method of venting blood from pulmonary trunk 77 is described in U.S. Pat. No. 4,889,137, which is incorporated herein by reference. In the technique described therein, a catheter is positioned from the interior jugular vein in the neck through the right atrium, right ventricle, and pulmonary valve into the pulmonary artery 77. The catheter has a coil about its periphery which holds the pulmonary valve open so as to drain blood from pulmonary trunk 77, thereby decompressing the left side of the heart.

For purposes of arresting cardiac function, an aortic occlusion catheter 82 is positioned in a femoral artery 84 by a percutaneous technique such as the Seldinger technique, or through a surgical cut-down 86. The aortic occlusion catheter 82 is advanced, usually over a guidewire (not shown), until an occlusion balloon 88 at its distal end is disposed in the ascending aorta 90 between the coronary ostia 92 and the brachiocephalic artery 94. Blood may be vented from ascending aorta 90 through a port 95 at the distal end of the aortic occlusion catheter 82 in communication with an inner lumen in aortic occlusion catheter 82, through which blood may flow to proximal end 96 of catheter 82. The blood may then be directed to a blood filter/recovery system 98 to remove emboli, and then returned to the patient's arterial system via CPB system 76.

When it is desired to arrest cardiac function, occlusion balloon 88 is inflated by injecting inflation fluid, usually a mixture of saline and a radiographic contrast agent, from a syringe 100 connected to proximal end 96 of catheter 82, through an inflation lumen in catheter 82 to the interior of occlusion balloon 88. Occlusion balloon 88 is expanded until it completely occludes ascending aorta 92, blocking blood flow therethrough. A cardioplegic fluid such as potassium chloride (KCl) is then delivered to the myocardium in one or both of two ways. Cardioplegic fluid may be delivered in an anterograde manner from a cardioplegia pump 101 through an inner lumen in aortic occlusion catheter 82 and a port distal to occlusion balloon 88 into the ascending aorta upstream of occlusion balloon 88. The cardioplegic fluid is then infused into the coronary arteries and paralyzes the myocardium.

Alternatively, or in conjunction with such anterograde delivery, cardioplegic fluid may be delivered in a retrograde manner through a retroperfusion catheter 102 positioned in the coronary sinus 104. Retroperfusion catheter 102 may be positioned, usually over a guidewire (not shown), from the neck through the interior jugular vein 106 and superior vena cava 108, or from the groin through a femoral vein 72 and the inferior vena cava 74. Retroperfusion catheter 102 may have one or more balloons (not shown) at its distal end to enhance positioning and infusion of cardioplegia into the coronary sinus. Cardioplegic fluid may thus be infused through the coronary veins into the capillary beds, paralyzing the myocardium.

The right lung may be collapsed using known techniques. Usually, a tube is introduced through the trachea into the right main stem bronchus, and a vacuum is applied through the tube to collapse the lung.

With cardiopulmonary bypass established, cardiac function arrested, and the right lung collapsed, the patient is prepared for surgical intervention within the heart H. Referring again to FIG. 2, a surgical cutting instrument such as angled scissors 110, as well as a grasping instrument such as grasping forceps 112, are introduced through access cannula 22 or through trocar sleeves 24A, 24B. Angled scissors 110 and forceps 112 are used to form an opening in the pericardium, providing access to the right side of the left atrium.

Angled scissors 110 are illustrated more clearly in FIGS. 12A–12D. Angled scissors 110 include a shaft 114 having a distal end 116, a proximal end 118, and an actuator 120 attached to proximal end 118. Shaft 114 of angled scissors 110 has a length selected to allow intervention within left atrium LA of heart H, and is usually at least about 15 cm in length and preferably 20 cm to 35 cm in length. Actuator 120 includes a movable arm 122 pivotally coupled to a stationary arm 124. A linkage 126 connects movable arm 122 to a push rod 128 extending slidably through shaft 110. By pivoting movable arm 122 toward shaft 114, push rod 128 is translated distally. A stationary blade 130 is mounted to distal end 116 of shaft 114, and a movable blade 132 is pivotally mounted to stationary blade 130. Push rod 128 is linked to movable blade 132 such that distal movement of push rod 128 pivots movable blade 132 toward stationary blade 130. Blades 130, 132 may be mounted at various angles relative to shaft 114, as illustrated in FIGS. 12B–12D. A flush port (not shown) may also be provided in shaft 114 for delivering a flushing solution such as saline to distal end 116 to remove fluid and/or debris from blades 130, 132 or from the surgical site.

In addition to angled scissors 110, a retractable knife 134, illustrated in FIG. 13, may be used for various cutting purposes. Retractable knife 134 comprises a shaft 136 having a distal end 138 and a proximal end 140. A handle 142 is attached to proximal end 140, to which an actuator 144 is slidably mounted. A push rod (not shown) is coupled to actuator 144 and extends slidably through shaft 136. A knife blade 146 is slidably mounted at distal end 138 of shaft 136 and is linked to the push rod, such that sliding actuator 144 proximally retracts knife blade 146 within a sheath 148 mounted to distal end 138. Alternatively, knife blade 146 may be fixed to shaft 136, and sheath 148 slidably mounted to shaft 136 and linked to the push rod, such that sheath 148 may be retracted and extended over knife blade 146 by sliding actuator 144.

Grasping forceps 112 are illustrated in FIGS. 14A–14B. Grasping forceps 112 have a construction much the same as that of angled scissors 110, with an actuator 150 translating a push rod 152 slidably disposed in a shaft 154. A stationary jaw 158 is fixed to a distal end 156 of shaft 154, and a movable jaw 160 is slidably mounted to shaft 154. Push rod 152 is linked to movable jaw 160, such that translation of push rod 152 by actuator 150 closes movable jaw 160 against stationary jaw 158. Grooves or other textural features may be provided on the inner surfaces of jaw 158 and/or jaw 160 to improve grip upon tissue.

Figure 4:
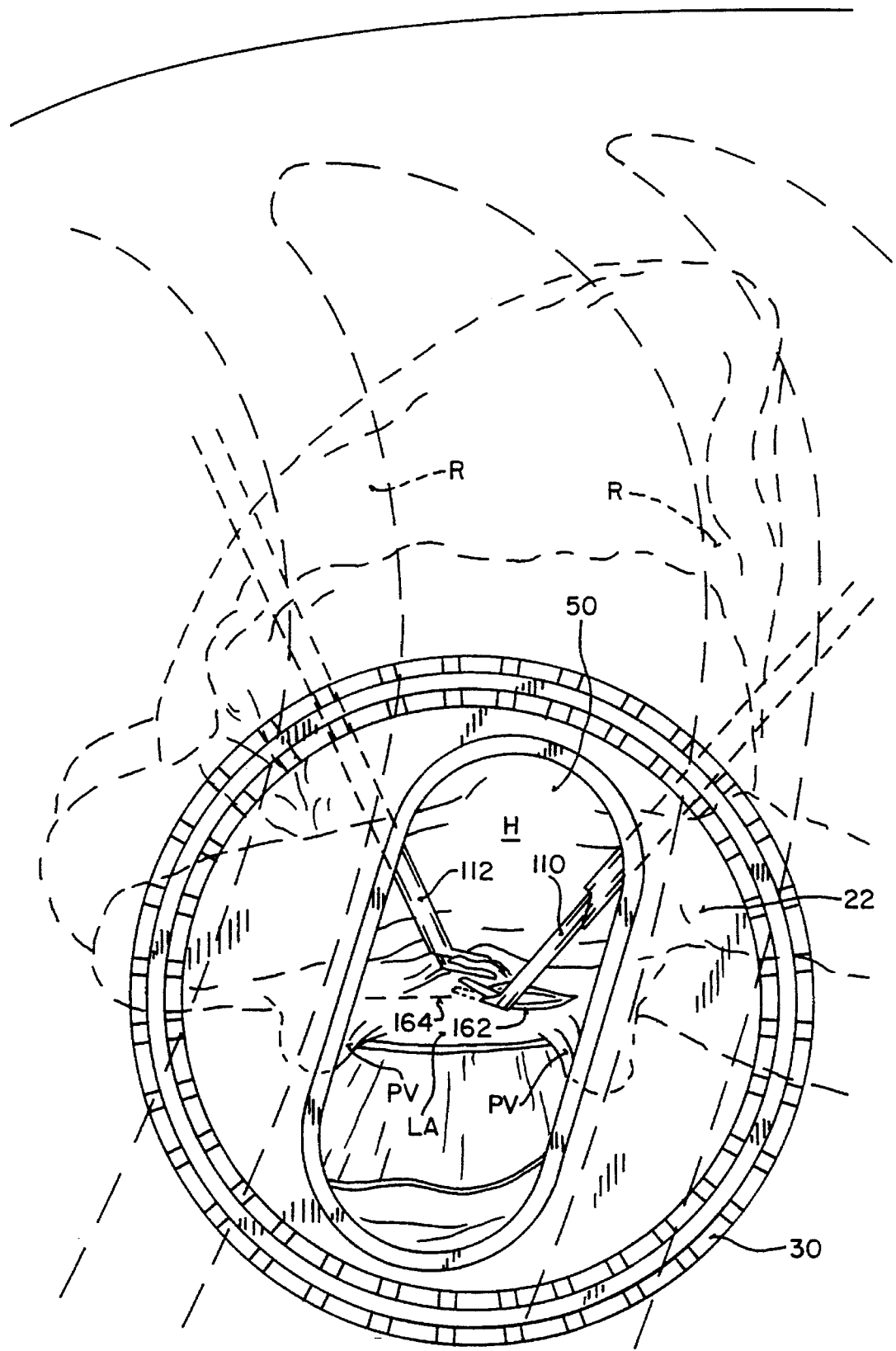
FIG. 4 is a top view looking into the patient's thoracic cavity through a passage of an access cannula in the system of FIG. 1, showing the creation of an atriotomy in the patient's left atrium.

FIG. 4 illustrates the view into the thoracic cavity through passage 50 of access cannula 22. Angled scissors 110 aided by grasping forceps 112 are shown cutting through the right side of left atrium LA to form an atriotomy 162. Atriotomy 162 is formed along dotted line 164 anterior to right pulmonary veins PV. A completed description of techniques for forming such an atriotomy is found in Kirklin and Barratt-Boyes, *Cardiac Surgery*, pp. 329–340, the disclosure of which has been incorporated herein by reference. Usually, atriotomy 162 will be formed under visualization by means of endoscope 25 (FIGS. 1 and 2), although direct viewing is possible through passage 50 of access cannula 22, or through a trocar sleeve 24.

Figure 5:
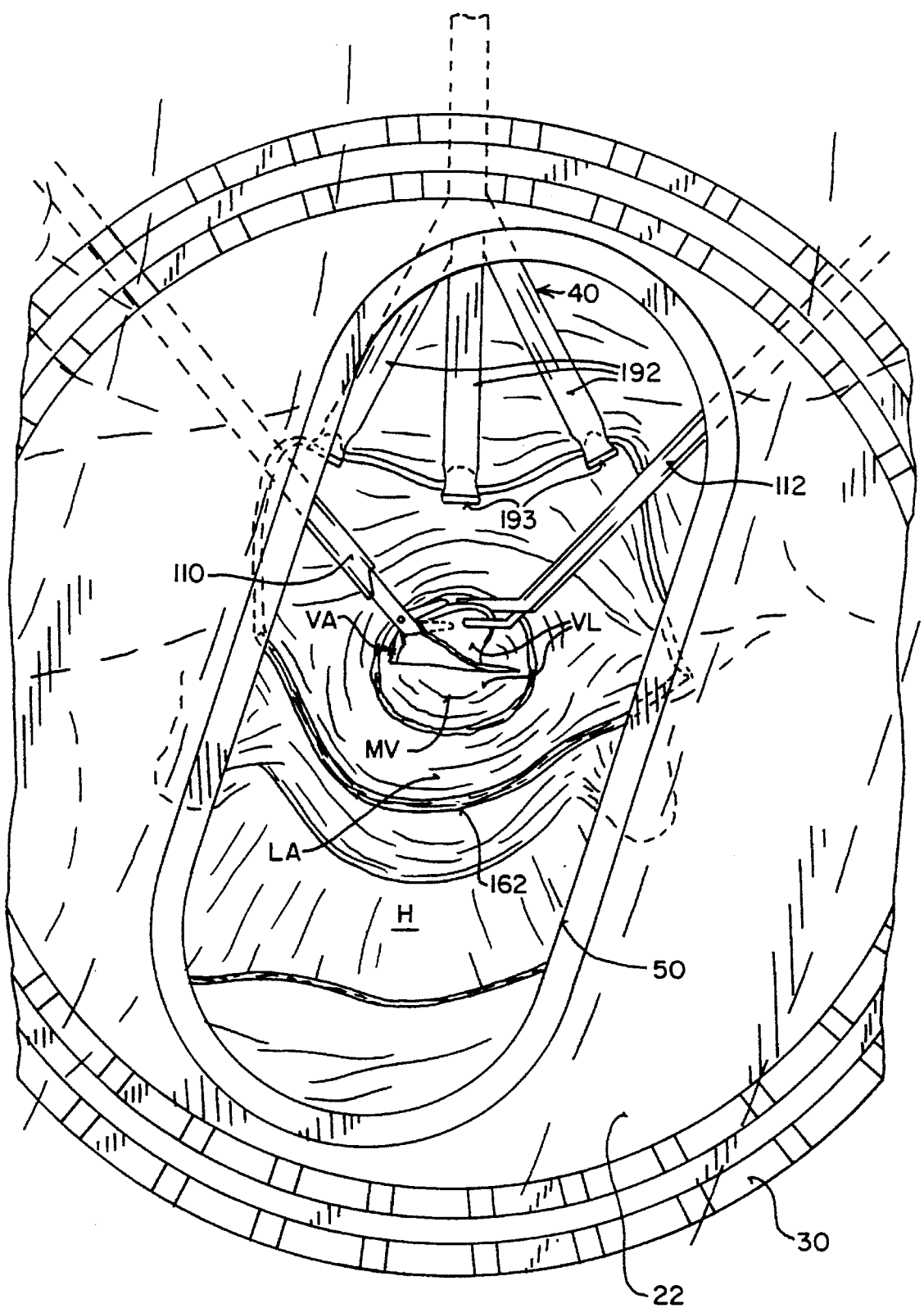
FIG. 5 is a top view looking into the patient's thoracic cavity through a passage of an access cannula in the system of FIG. 1, showing the removal of the mitral valve leaflets.
Figure 15:
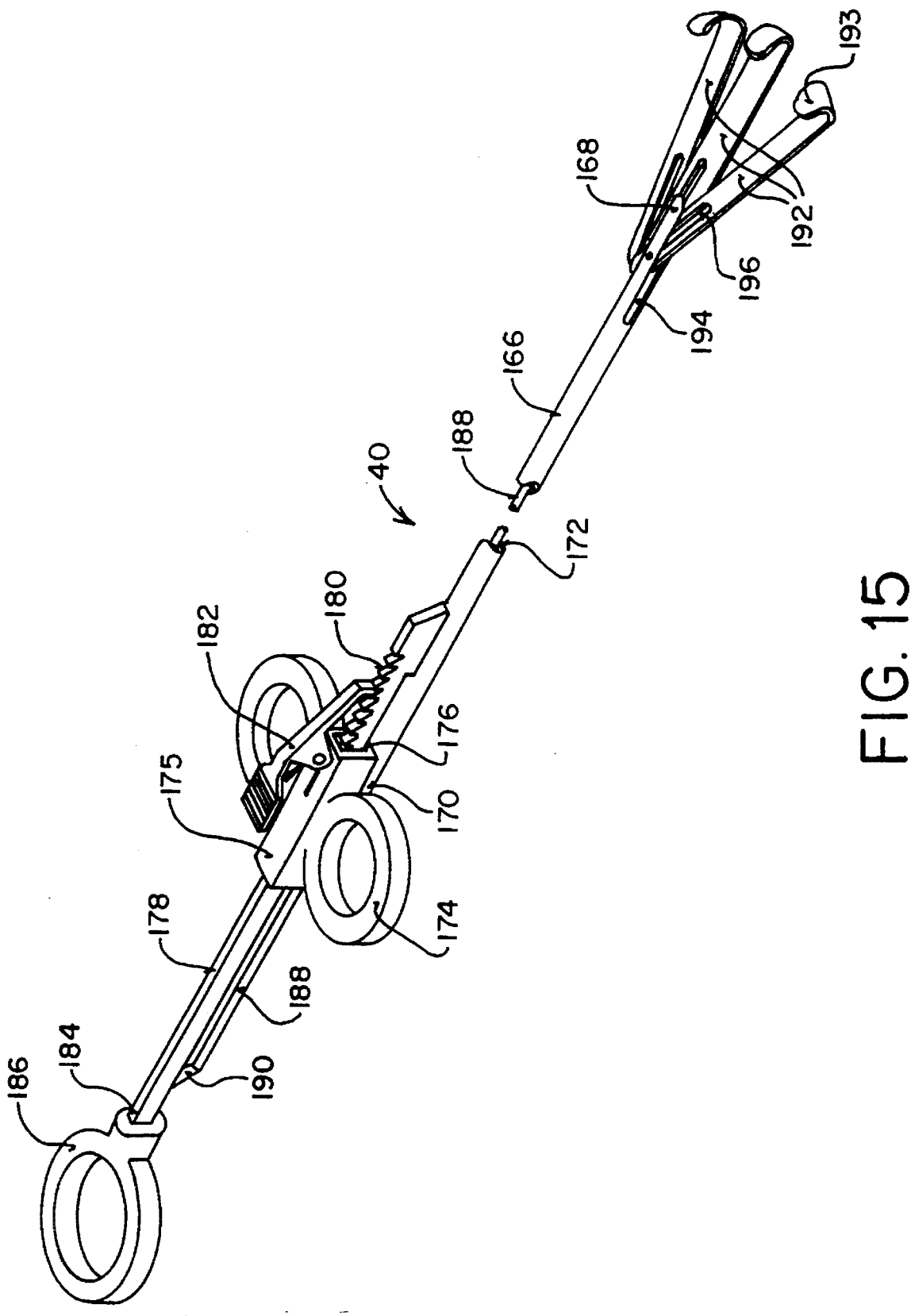
FIG. 15 is a perspective view of a left atrial retractor in the system of FIG. 1.

Upon completion of atriotomy 162, the wall of left atrium LA on the anterior side of atriotomy 162 is retracted anteriorly by means of thoracoscopic retractor 40, as illustrated FIGS. 1 and 5. Thoracoscopic retractor 40, illustrated more clearly in FIG. 15, includes a shaft 166 having a distal end 168, a proximal end 170, and an inner lumen 172 therebetween. A pair of finger rings 174 is mounted to proximal end 170 of shaft 166. A guide 175 is also mounted to proximal end 170 having a channel 176 extending therethrough. A sliding rod 178 extends through channel 176 and has a plurality of teeth 180 on a lateral surface thereof which are engaged by a pawl 182 pivotally mounted to guide 175 and biased by a spring (not shown) against teeth 180. Sliding rod 178 has a proximal end 184 to which a thumb ring 186 is attached, allowing thumb ring 186 to be drawn toward finger rings 174. A push rod 188 is slidably disposed in lumen 172 of shaft 166 and is attached at its proximal end 190 to sliding rod 178. Three rake arms 192 are pivotally coupled to shaft 166 within a transverse slot 194 at distal end 168. Rake arms 192 each have a hooked distal end 193 for engaging and retracting tissue. The distal end of push rod 188 slidably engages rake arms 192 within a slot 196 in each rake arm. In this way, by sliding push rod 188 distally, rake arms 192 collapse in an overlapping configuration suitable for introduction through one of trocar sleeves 24. Once rake arms 192 are introduced into the thoracic cavity, they may be expanded by pulling thumb ring 186 relative to finger rings 174.

Referring again to FIG. 5, retractor 40 is introduced into the thoracic cavity through trocar sleeve 24 and rake arms 192 are deployed into their expanded configuration. Retractor 40 is manipulated so that hooked ends 193 of rake arms 192 engage the wall of left atrium LA on the anterior side of atriotomy 162. Retractor 40 is then pulled in the anterior direction to retract the wall of left atrium LA, opening atriotomy 162 and exposing the patient's mitral valve MV within the left atrium LA. A conventional stopcock, cam lock, or other clamping device (not shown) may be provided on trocar sleeve 24 to lock retractor 40 in position, or shaft 166 may be provided with an adjustable collar (not shown) for engaging trocar sleeve 24 to maintain retractor 40 in position.

Figure 26:
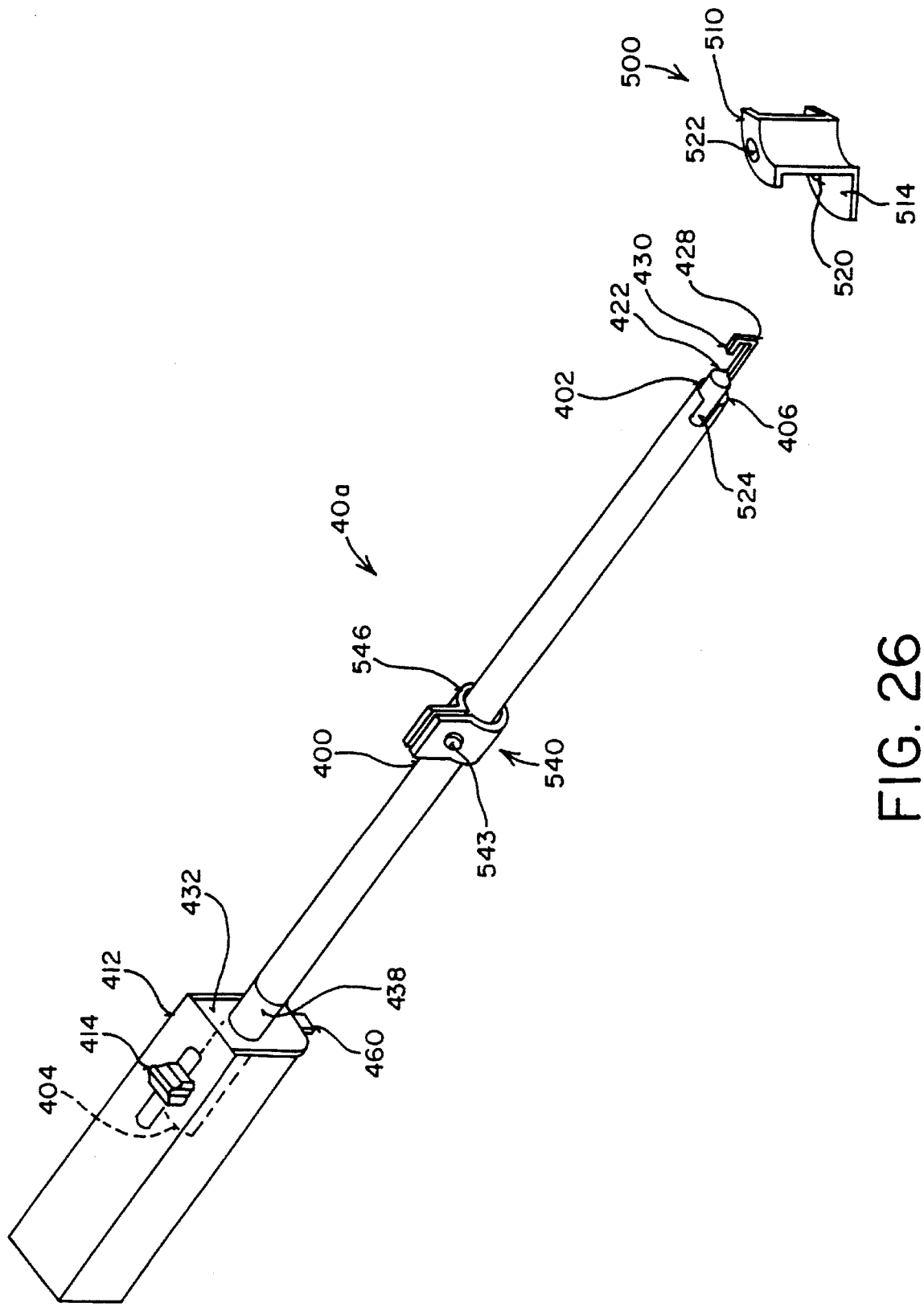
FIG. 26 is a perspective view of an alternative embodiment of a retractor suitable for retracting the left atrium according to the invention.

FIG. 26 illustrates an alternative embodiment of thoracoscopic retractor 40. Retractor 40a includes a shaft 400 having a distal end 402 and a proximal end 404. Shaft 400 is preferably a stainless steel tube having an outer diameter less than 5 mm so as to fit within a cannula having an internal diameter less than 8 mm. Shaft 400 has a length selected to reach a target site in a body cavity, such as the heart, and to extend sufficiently out of the body cavity to facilitate easy manipulation of retractor 40a with distal end 402 positioned in or near the body structure. Thus, shaft 400 should have a length of 10–40 cm and preferably 15–30 cm. It should be noted that although shaft 400 is shown as having a circular cross-sectional shape in the drawings, shaft 400 could also have a rectangular, oval, channel or other cross-sectional shape.

Figure 27D:
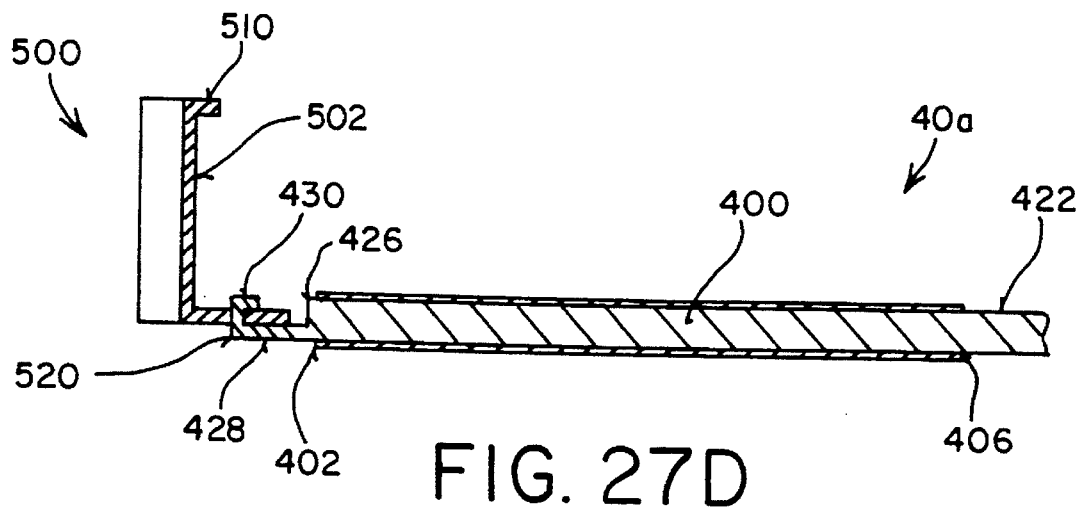
FIGS. 27C–27D are side cross-sectional views of proximal and distal portions, respectively, of the retractor of FIG. 26 in a releasable position on the tissue supporting member of FIGS. 27A–27B.
Figure 27B:
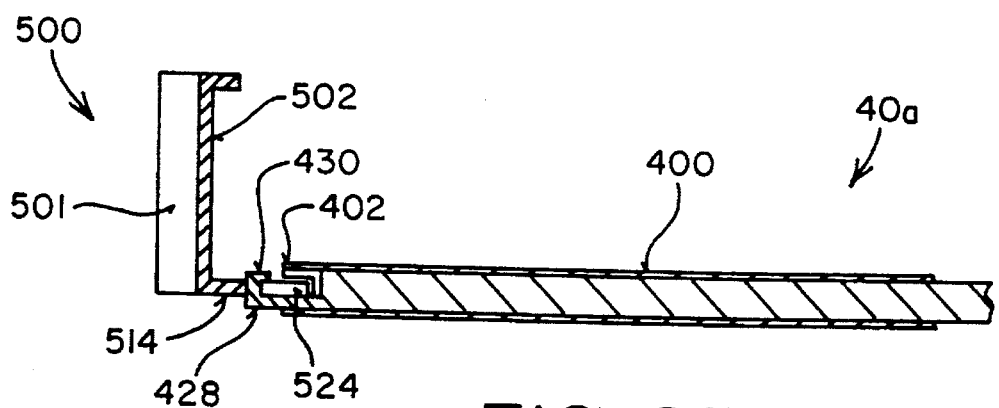
FIGS. 27A–27B are side cross-sectional views of proximal and distal portions, respectively, of the retractor of FIG. 26 in a locked position on a tissue supporting member.
Figure 27C:
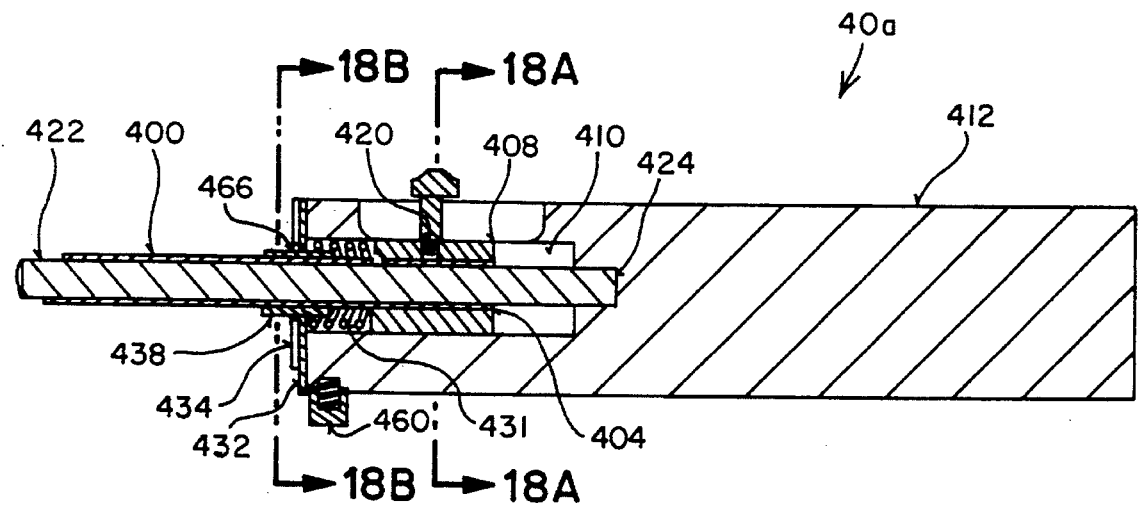
Figure 27A:
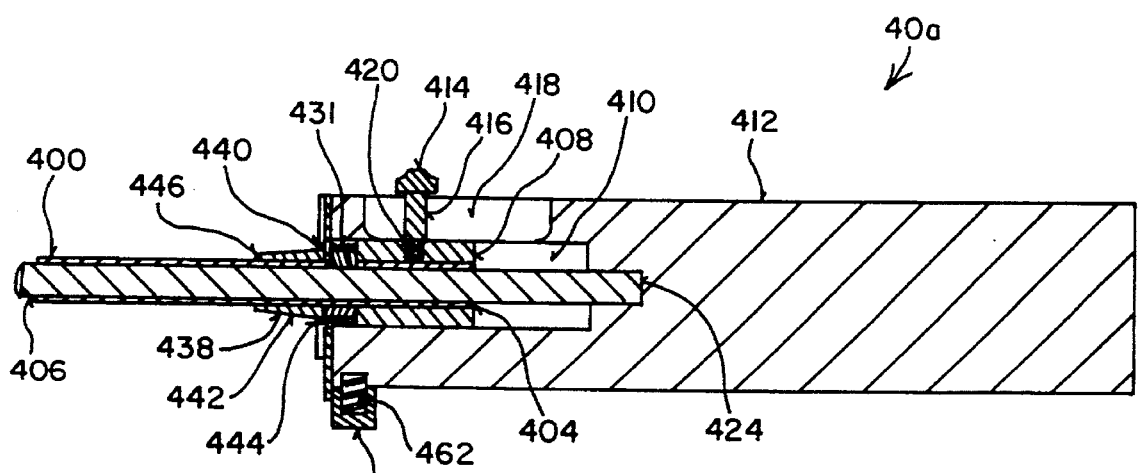

FIGS. 27A–27D illustrate proximal and distal portions of retractor 40a holding a tissue supporting member 500, described in further detail below. Referring to FIG. 27A, shaft 400 has an axial passage 406 extending from distal end 402 to proximal end 404. Proximal end 404 of shaft 400 is fixed to a handle 412. An outer tube 408 is slidably disposed within an annular bore 410 in handle 412. An actuator slide 414 has a lower arm 416 projecting into a longitudinal slot 418 in handle 412 and fixed to outer tube 408 by a screw 420. Lower arm 416 of slide 414 is axially movable within slot 418 so that shaft 400 may slide together with slide 414 relative to handle 412. Note that although an actuator in the form of a sliding knob has been described in a preferred embodiment, various types of actuator mechanisms may be used to slide shaft 400 with respect to handle 412, including, for example, a plunger mechanism, a pair of scissor type handles, or a rotatable knob that converts rotational motion into axial motion. In addition, the actuator mechanism could be similar to that disclosed in commonly assigned U.S. Pat. No. 5,501,698, which is incorporated herein by reference.

As shown in FIGS. 27C and 27D, rod 422 extends through axial passage 406 of shaft 400 and has proximal and distal ends 424, 426. Rod 422 may be solid or, if desired, could include one or more axial lumens for fluid delivery or other purposes. Referring to FIG. 27C, proximal end 424 of rod 422 is fixed to handle 412 so that shaft 400 is slidable relative to rod 422. Referring to FIG. 27D, distal end 426 of rod 422 has a hook 428 forming a U-shaped tip 430. U-shaped tip 430 facilitates the engagement of hook 428 with an opening in tissue supporting member 500 (discussed in further detail below). Hook 428, however, could have a tip with an L-shape, a V-shape or a variety of other shapes so long as the tip is configured to engage a portion of tissue supporting member 500.

Axial movement of shaft 400 with respect to hook 428 moves hook 428 between a locked position (FIGS. 27A–B), where hook 428 is disposed close to distal end 402 of shaft 400, and a releasable position (FIGS. 27C–D), where hook 428 is disposed further away from distal end 402 of shaft 400. As shown in FIG. 27C, a compression spring 431 is disposed between a front plate 432 in handle 412 and outer tube 408 to bias shaft 400 proximally into the releasable position.

Figure 28A:
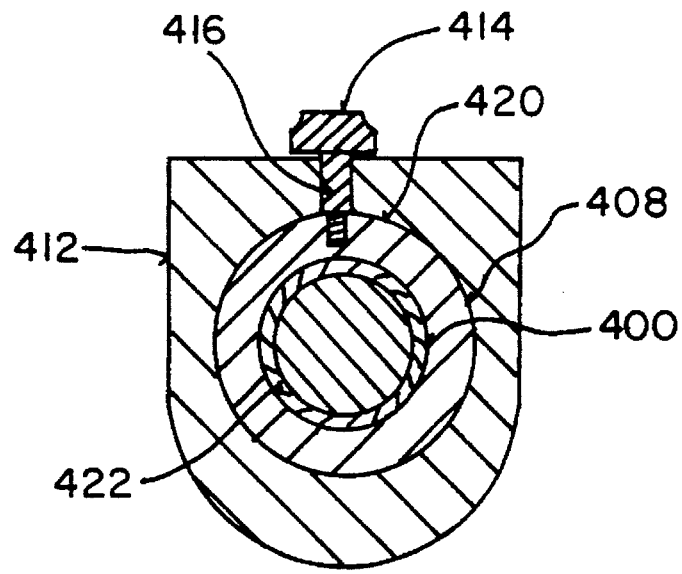
FIGS. 28A–28B are transverse cross-sectional views of the retractor of FIG. 26 taken substantially along the plane of the lines 28A and 28B, respectively, in FIG. 27C.
Figure 28B:
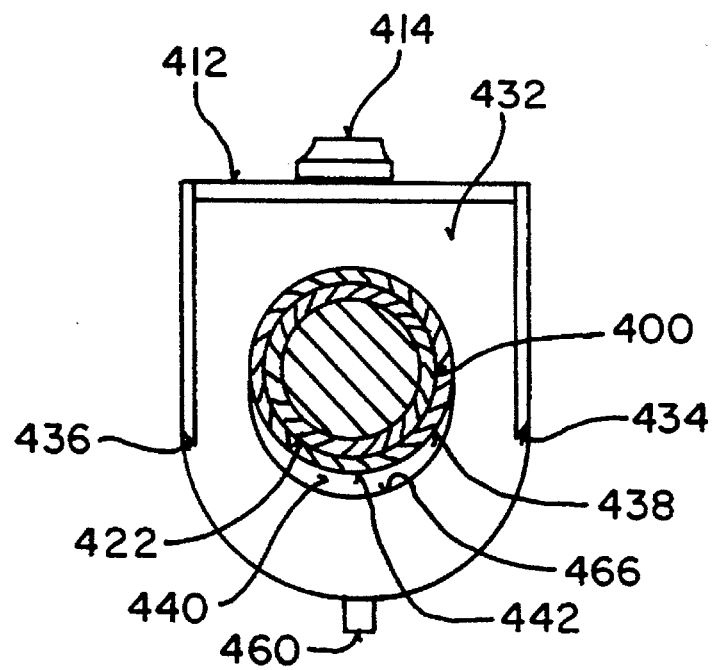

Referring to FIG. 28B, front plate 432 is slidably disposed within transverse slots 434, 436 at the distal end of handle 412. Note that plate 432 may, if desired, be completely housed within handle 12. A circular hole 440 is disposed in front plate 432. As shown in FIG. 27A, sleeve 438 is fixed to shaft 400 and has an outer surface 442 that tapers in the distal direction so that sleeve 438 has a larger radius at a proximal end 444 than at a distal end 446. The radius of proximal end 444 of sleeve 434 is slightly less than the radius of circular hole 440 in plate 432. Plate 432 is slidable in a direction perpendicular to the axial direction between the position in FIG. 27C, where hole 440 is aligned with proximal end 444 of sleeve 438, and the position in FIGS. 27A and 28B, where hole 440 is not aligned with proximal end of sleeve 438. A button 460 is fixed to plate 432 and is biased outwardly by a compression spring 462 so that plate 432 is urged into the closed position, as shown in FIG. 27A.

Pushing down on button 460 moves plate 432 into the position shown in FIG. 27C so that sleeve 438 may enter annular bore 410. This allows outer tube 408 and shaft 400 to move proximally into the releasable position under the force of spring 431. To move shaft 400 back into the locked position of FIG. 27A, the user moves actuator slide 414 in the distal direction thereby driving shaft 400 and sleeve 438 in the distal direction relative to handle 412. Inner circumferential surface 466 of hole 440 will slide along the tapered outer surface 442 of sleeve 438 until sleeve 438 exits annular bore 410. Once proximal end 444 of sleeve 438 is distal to hole 440, compression spring 462 will urge plate 432 into the closed position thereby locking sleeve 438 and shaft 400 in the locked position of FIGS. 27A and 27B.

Figure 29A:
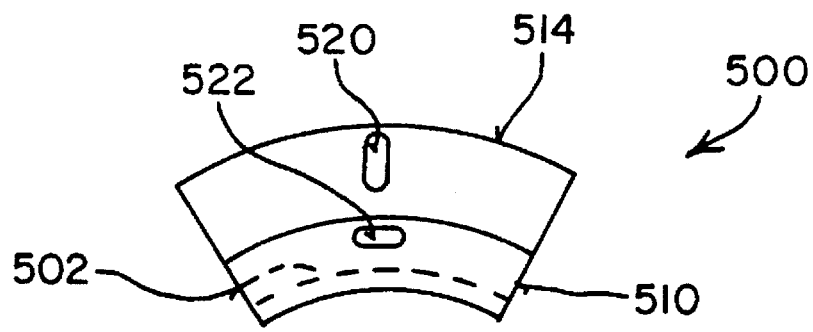
FIGS. 29A–29B are side and top views, respectively, of the tissue supporting member of FIGS. 27A–27D.
Figure 29B:
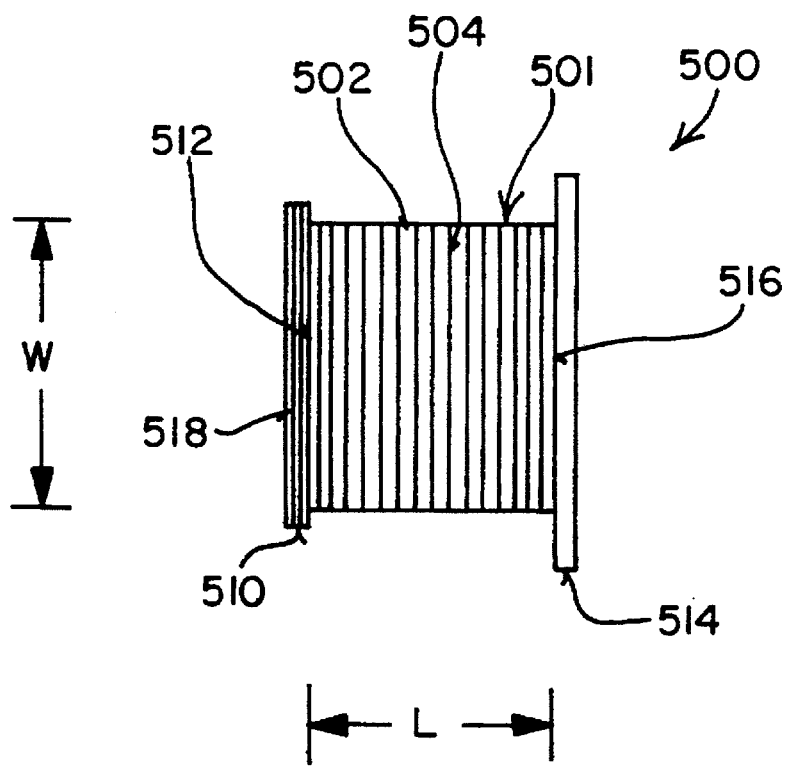

FIGS. 29A and 29B illustrate a preferred embodiment of a tissue supporting member 500 according to the invention. Tissue supporting member 500 includes a support plate 501 with an arcuate contact surface 502 configured for supporting a tissue structure thereon. Contact surface 502 may include grooves 504 to frictionally engage the tissue structure. Contact surface 502 preferably has a curvature selected to conform to an opening in a tissue structure. Preferably, the curvature of contact surface 502 defines an arc of a circle having a radius of 10–40 mm. This curvature facilitates the engagement of the tissue structure and is particularly useful for engaging the inner surface of an opening in a vessel or organ, such as atriotomy 262 in the atrial wall AW. It will be understood that contact surface 502 could have a variety of curvatures and could be flat. A curved surface is preferred, however, because it provides the least traumatic configuration for engaging the tissue structure and is effective at retaining the tissue structure without slippage.

Contact surface 502 preferably has a length L of 10–60 mm and more preferably 25–40 mm. Thus, contact surface 502 will extend relatively deeply beneath the tissue structure, and may support a relatively thick outer wall of a vessel or organ. As discussed below, this configuration is particularly useful for retraction of the atrial wall AW of the heart H because contact surface 502 is long enough to extend beneath the interatrial septum to prevent it from sagging or collapsing into the atrium when the opening is enlarged.

Contact surface 502 preferably has a width W of 10–50 mm and more preferably 20–40 mm to allow the surgeon to retract a large area of tissue, or to substantially enlarge an opening in a vessel or organ. This is advantageous when surgical instruments must be passed through the opening to perform procedures within the inner cavity of the tissue structure. It should also be understood that the size and shape of contact surface 502 will vary depending on the size of the individual patient and the particular tissue structure to be retracted.

Tissue supporting member 500 further includes a first lip 510 on a first end 512 of support plate 501 and a second lip 514 on a second end 516 of support plate 501. First lip 510 projects upwards from support plate 501 to retain the tissue structure on contact surface 502. First lip 510 may also include grooves 518 for frictionally engaging the tissue wall. Second lip 514 is preferably either perpendicular or at an acute angle to contact surface 502 to facilitate connection with shaft 400, discussed below.

Figure 29C:
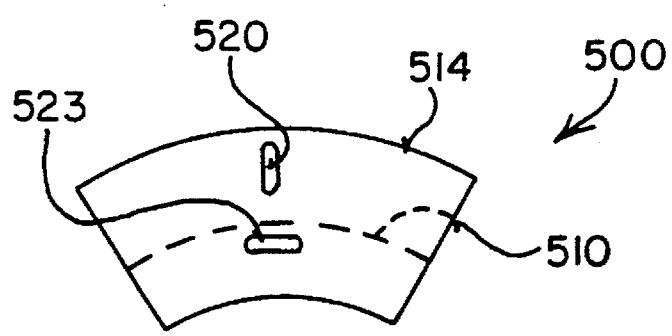
FIG. 29C is a side view of an alternative embodiment of the tissue supporting member of FIGS. 27A–27D.

A first opening 520 is formed in second lip 514 and a second opening 522 is formed in first lip 510. First and second openings 520, 522 both have generally oval shapes configured for receiving hook 428 of retractor 40a, as described below. Note that first and second openings 520, 522 may also be enlarged on one end to facilitate the engagement of hook 428 within openings 520, 522. In an alternative embodiment, tissue support member may further include a third opening 523 in second lip 514, as shown in FIG. 29C, or in first lip 510 (not shown). Third opening 523 is also configured for receiving hook 428 of retractor 40a.

FIGS. 27B and 27D illustrate tissue supporting member 500 releasably connected to hook 428 of retractor 40a. As shown in these figures, hook 428 engages first opening 520 such that contact surface 502 is oriented transversely to shaft 400. Preferably, contact surface 502 is at an angle of at most about 110°, and usually no more than 90° relative to the longitudinal axis of shaft 400. This configuration facilitates the support of a tissue wall on contact surface 502 when retractor 40a is moved in the proximal direction. In addition, grooves 504 provide frictional engagement of the tissue wall to further assist the retention of the tissue wall on contact surface 502.

To lock tissue supporting member 500 to retractor 40a, U-shaped tip 430 is moved into first opening 520 and shaft 400 is slid in the distal direction with respect to hook 428 in the manner described above. Distal end 402 of shaft 400 has two slots 524 formed on either side of U-shaped tip 430 to receive the edge of second lip 514 (most clearly illustrated in FIG. 26). As shown in FIG. 27B, tissue supporting member 500 is thereby rigidly secured to shaft 400 so that tissue supporting member 500 will be prevented from substantial rotation or translation relative to shaft 400 when hook 428 is in the locked position. This facilitates the surgeon's control of the tissue structure when manipulating retractor 40a.

Tissue supporting member 500 can also be connected to retractor 40a by engaging second opening 522 with hook 428. In this configuration, contact surface 502 is generally parallel to the longitudinal axis of shaft 400 to minimize the cross-sectional profile of retractor 40a and tissue supporting member 500 for introduction through a percutaneous penetration of minimum size. As shown in FIG. 29A, second opening 522 has a generally oval shape that is rotated 90 degrees with respect to first opening 520. Therefore, retractor 40a will be rotated 90 degrees (with respect to its orientation in FIGS. 27A–D) to slide U-shaped tip 430 through second opening 522. First and second openings 520, 522 are configured for being simultaneously held by two retractors 40a or other endoscopic instruments. The two retractors 40a will be generally perpendicular to each other when holding tissue supporting member 500 in first and second openings 520, 522.

It will be noted that tissue supporting member 500 is not limited to a support plate 501 with an arcuate contact surface 502 and can be a variety of conventional supporting members. For example, tissue supporting member 500 could include a pair of arms or hooks extending transversely from distal end 402 of shaft 400 and having distal tips that curve upwards to prevent the tissue wall from sliding off the contact surfaces. The arms could be movable into an open position where the arms are disposed apart from each other to form a "V" shape so that the surgeon can retract a substantial portion of the tissue wall. Tissue supporting member 500 could also be an annular ring with a circular upper contact surface that is oriented transversely to shaft 400.

Alternatively, tissue supporting member 500 could comprise an expandable member, such as a balloon, that can be inflated into an enlarged configuration for supporting the tissue structure. In the enlarged configuration, the balloon should be large enough to substantially enlarge the opening in the tissue structure and to extend beneath the tissue structure to support the outer wall. To expand the balloon, shaft 400 would further include a lumen fluidly coupling the balloon with an inflation means at proximal end 404 of shaft 400.

Figure 30:
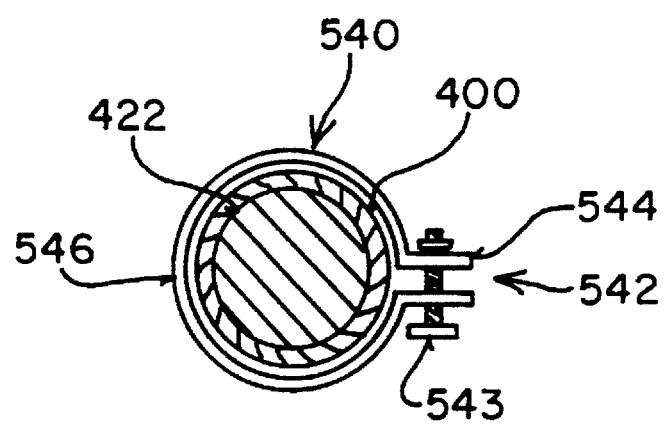
FIG. 30 is a transverse cross-sectional view of the retractor of FIG. 26 with an adjustable collar for clamping the retractor in a longitudinal position with respect to a percutaneous penetration.

The invention may further include means for clamping shaft 400 in a longitudinal position with respect to a percutaneous penetration in the patient. Referring to FIG. 30, an adjustable collar 540 is slidably disposed on shaft 400. Collar 540 includes clamping means 542, which may comprise a bolt 543 threadably coupled to a split extension 544 of an annular ring 546. Bolt 543 can be rotated to tighten or loosen collar 540 on shaft 400. Note that other types of clamping means may be used, such as a cam lock, set screw or other conventional means. Alternatively, annular ring 546 could comprise outer threads around its circumference that mate with inner threads of a clamping ring. Rotation of the clamping ring around annular ring 546 would tighten or loosen collar 540 around shaft 400.

Preferably, collar 540 has an outer diameter greater than 10 mm, usually 20–30 mm, so that collar 540 will not pass through a percutaneous penetration or access cannula having a diameter of 10 mm or less. With this configuration, collar 540 can be placed against the surface of the patient's body or the end of an access cannula in the locked position to prevent shaft 400 from moving in the distal direction.

The invention is not limited to the clamping means described above. For example, shaft 400 can be inserted into a locking cannula (not shown) having a stopcock, cam lock or other clamping means for closing an inner lumen of the cannula onto shaft 400 thereby securing its position with respect to the tissue structure. Alternatively, handle 412 may be held by a clamp (not shown) or other suitable means secured to a fixed object outside of the patient's body, such as the operating table or a scope holder.

Alternatively, a fixed clamp system, such as a wishbone retractor system, can be used to hold shaft 400. This known system is advantageous because it holds shaft 400 above the patient so that a torque can be applied on shaft 400 without causing trauma to the patient. In addition, more than one shaft 400 may be held by this type of system so that more than one retractor 40a can be used to retract the tissue structure. A suitable wishbone retractor system is commercially available at Pilling Surgical Instruments of Fort Washington, Pa. under the brand name "Abdominal Vascular Set".

Figure 31A:
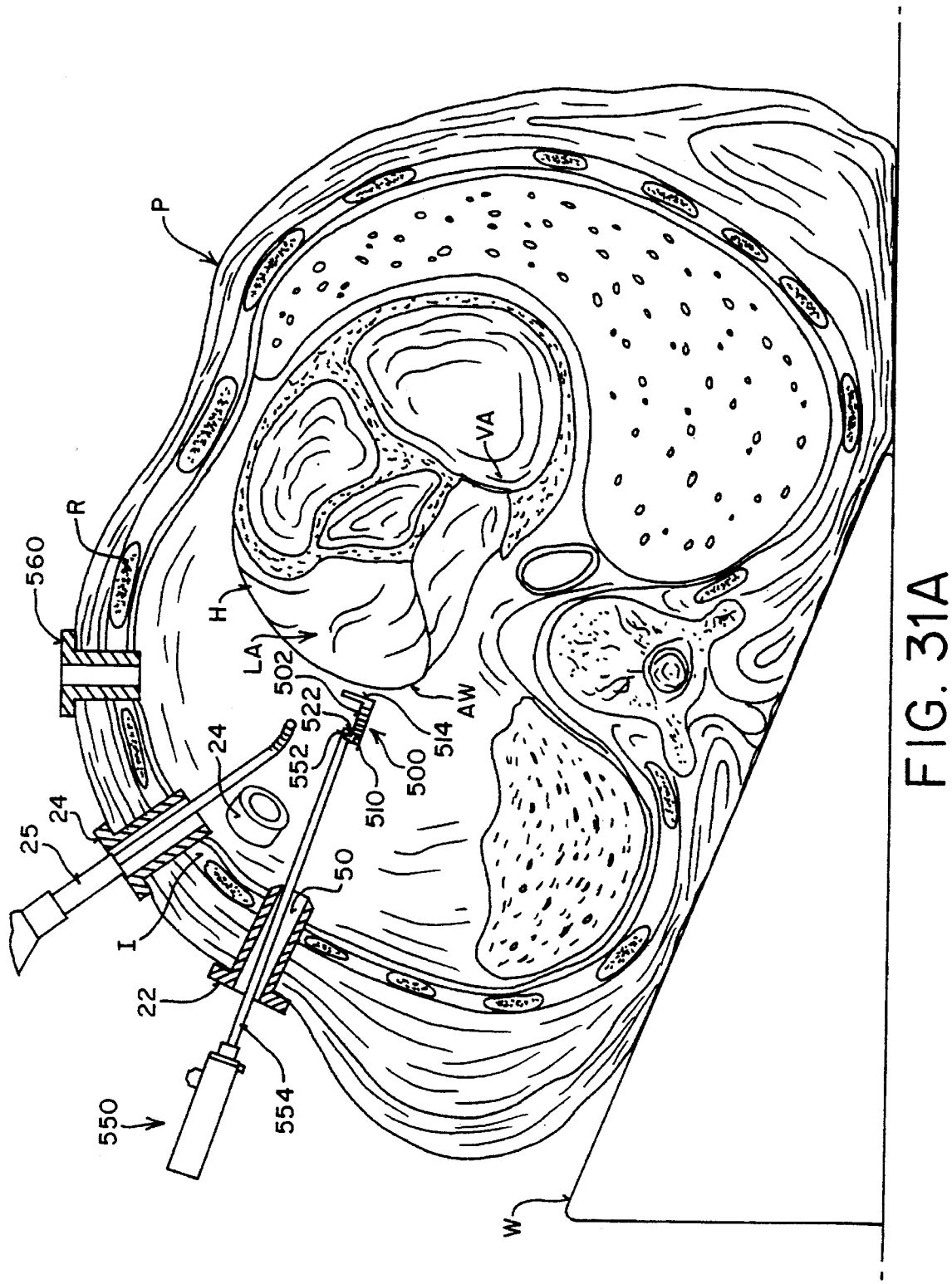
FIGS. 31A–31D are transverse cross-sectional views of the system and patient of FIG. 1, taken through the patient's thorax, showing the introduction of the tissue supporting member of FIGS. 27A–27D through an access cannula, the connecting of the tissue supporting member to the retractor of FIG. 26 within the thoracic cavity and the retraction of the patient's left atrium wall.

FIGS. 31A–31D illustrate a method for retracting the outer wall AW of the left atrium LA with retractor 40a and tissue supporting member 500. Referring to FIG. 31A, an introducer 550 is used to introduce tissue supporting member 500 through access cannula 22 in the right lateral portion of the patient's chest. Introducer 550 may be identical to retractor 40a described above. However, introducer 550 may also be a variety of conventional endoscopic devices such as forceps, graspers, retractors or clamp applicators.

Introducer 550 has a hook 552 slidably coupled to a shaft 554 for releasably holding tissue supporting member 500. Hook 552 is received within second opening 522 in first lip 510 so that contact surface 502 is generally parallel to the longitudinal axis of shaft 554. This facilitates introduction through passage 50 of access cannula 22 and allows tissue supporting member 500 to be positioned at a suitable location within the thoracic cavity for connection to retractor 40a, as discussed below. Access cannula 22 has been positioned so that instruments introduced therethrough may be directed toward the right side of the left atrium LA of heart H, as discussed above. To accommodate the introduction of replacement valve 36, passage 50 will have a cross-sectional width of about 12–20 mm and a cross-sectional height of about 25–50 mm, preferably 30–40 mm. To fit tissue supporting member 500 through access cannula 22, width W is preferably aligned with the cross-sectional height of access cannula 22, as shown in FIG. 31A.

Figure 31B:
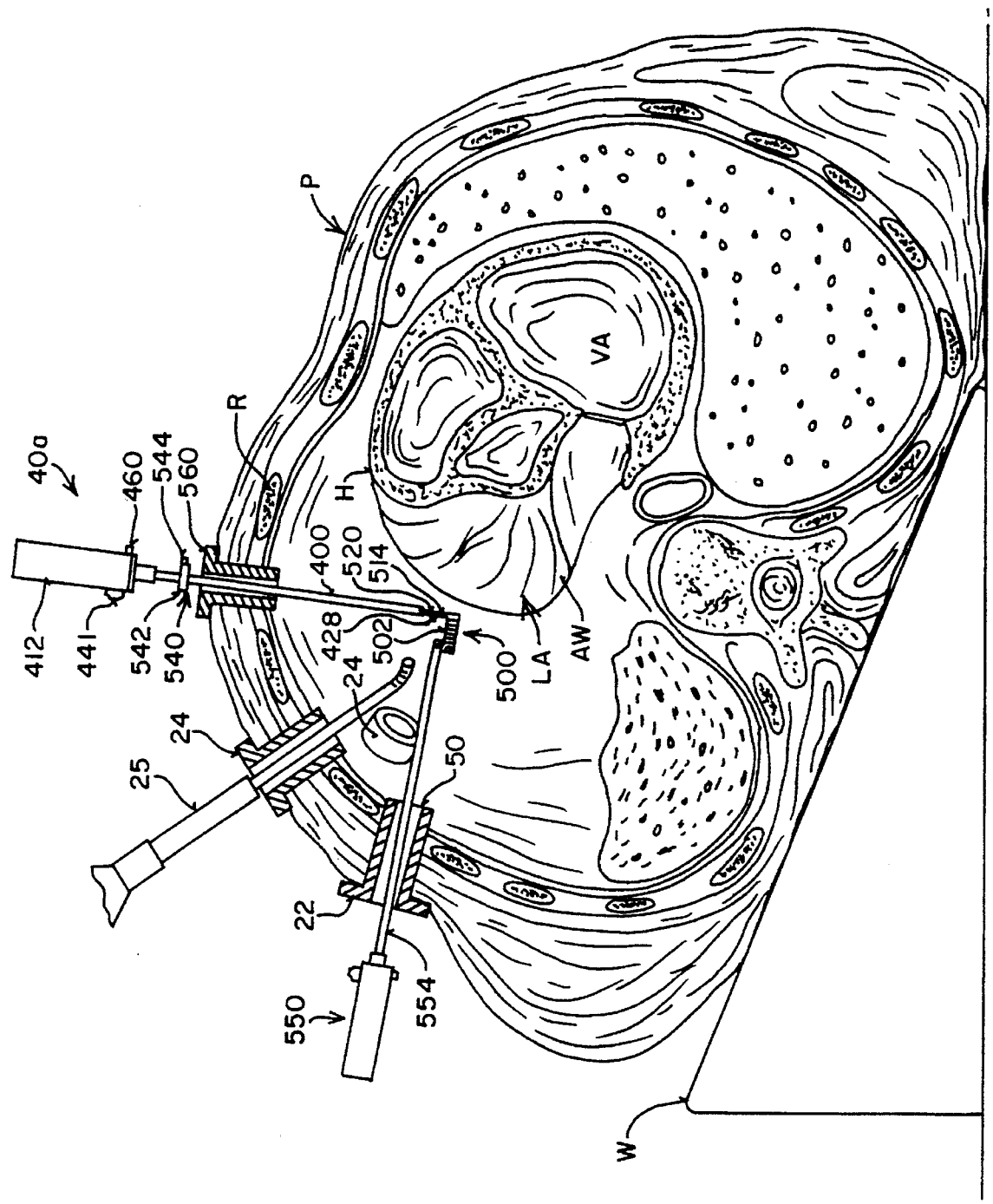

Referring to FIG. 31B, retractor 40a is introduced through a second percutaneous intercostal penetration in the anterior side of the patient's chest, preferably just to the right of the sternum and anterior to the right lateral side of the heart H. Usually, a trocar sleeve or other cannula 560 having a diameter less than 5 mm is positioned in the second intercostal penetration. As discussed above, the anterior side of the chest contains many nerves that could be damaged by creating a large opening. In addition, the intercostal spaces between the patient's ribs are smaller in this region of the chest. Therefore, a smaller incision is desirable. It should be noted, however, that the invention is not limited to a cannula or incision having a diameter of less than 5 mm and retractor 40a could be introduced through a much larger intercostal incision, if necessary.

Figure 6:
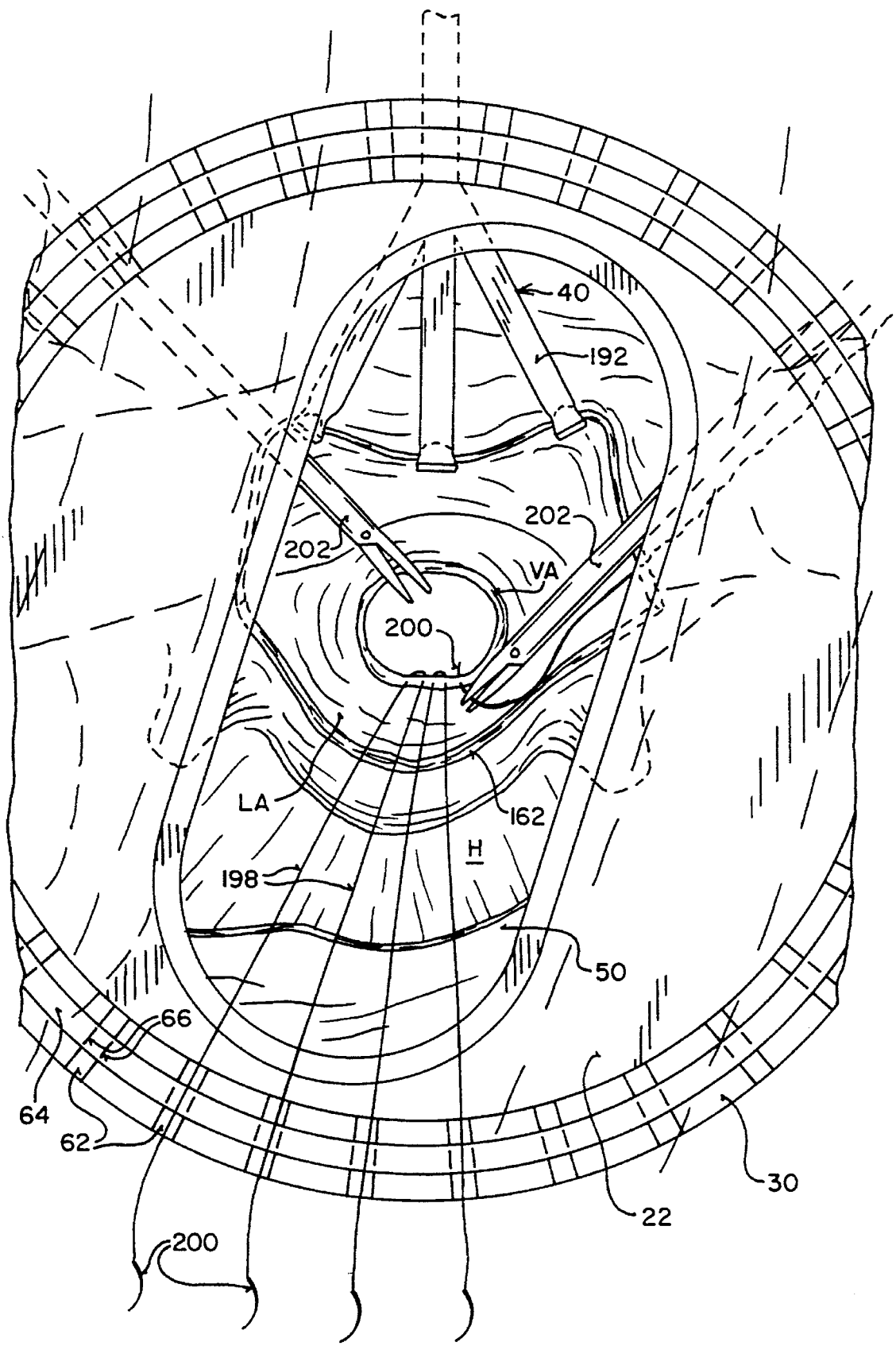
FIG. 6 is a top view looking into the patient's thoracic cavity through a passage of an access cannula in the system of FIG. 1, showing the application of sutures to the mitral valve annulus.

Once retractor 40a has been introduced through cannula 560, hook 428 is moved through first opening 520 in second lip 514 of tissue supporting member 500 while tissue supporting member 500 is held with introducer 550. The surgeon then moves actuator knob 441 in the distal direction to slide shaft 400 distally with respect to hook 428 thereby locking tissue supporting member 500 to retractor 40a. As illustrated in FIG. 31B, tissue supporting member 500 has been positioned generally perpendicular to retractor 40a to facilitate the connection of shaft 400 and tissue supporting member 500. Usually, tissue supporting member 500 will be connected to retractor 40a under visualization by means of endoscope 25, although direct viewing is possible through passage 50 of access cannula 22 (FIGS. 4–6).

Figure 31C:
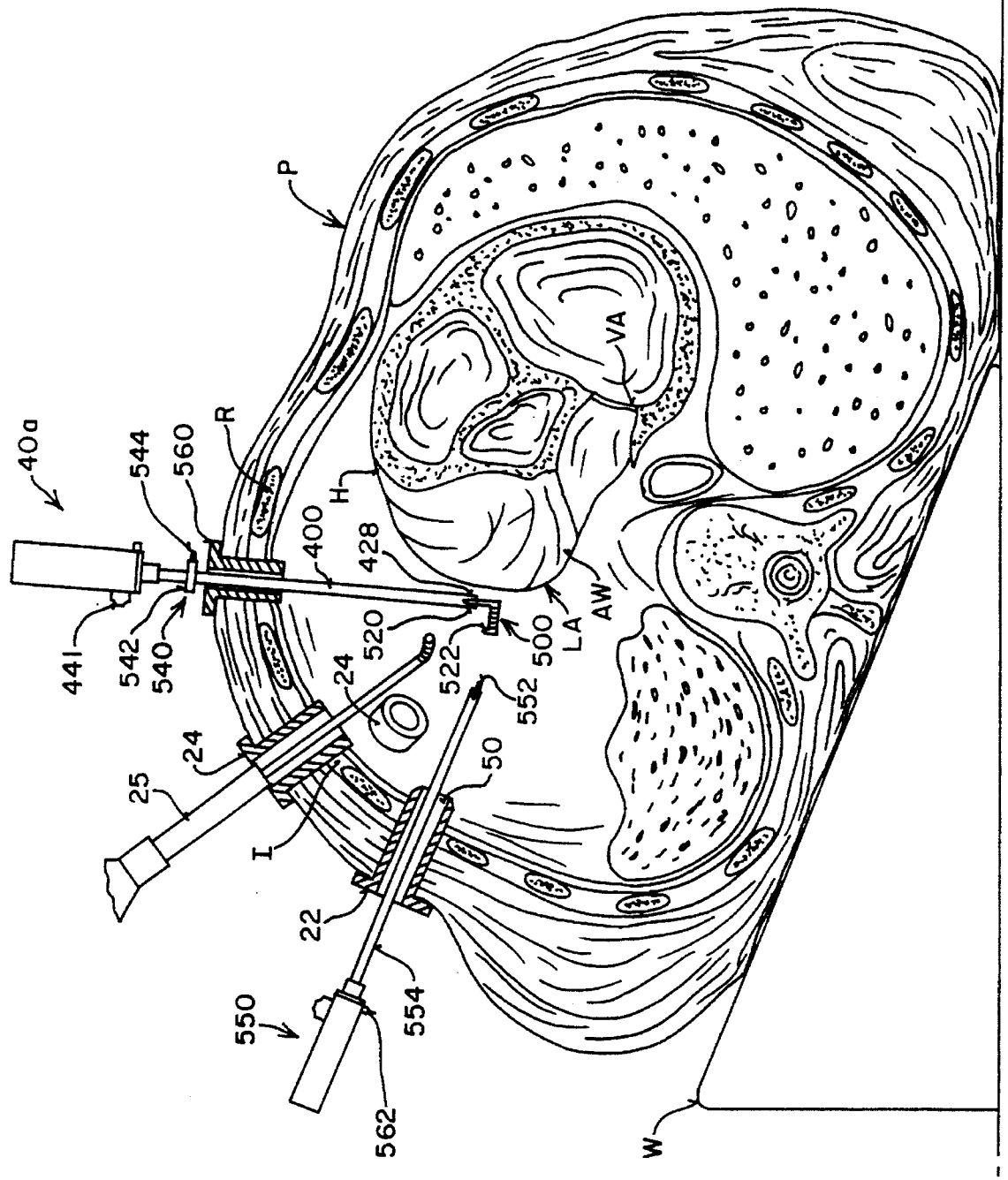

At this point, introducer 550 is preferably withdrawn from the thoracic cavity, as shown in FIG. 31C, so that other suturing and cutting instruments may be introduced through access cannula 22 for the mitral valve operation. To disengage introducer 550 from tissue supporting member 500, a button 562 on introducer 550 (similar to button 460 on retractor 40a) is pushed to slide shaft 554 in the proximal direction with respect to hook 552. The surgeon then manipulates introducer 550 to disengage hook 552 from second opening 522 and withdraws introducer 550 from the thoracic cavity.

It should be noted that the invention is not limited to a single retractor 40a for supporting atrium wall AW. For example, another intercostal penetration may be made in the anterior side of the patient's chest for introduction of a second retractor shaft (not shown). In this configuration, introducer 550 can be used to introduce a second tissue supporting member through access cannula 22 and into the thoracic cavity for attachment to the second retractor shaft. Both tissue supporting members can then be positioned to retract atrium wall AW, as is described below.

Figure 31D:
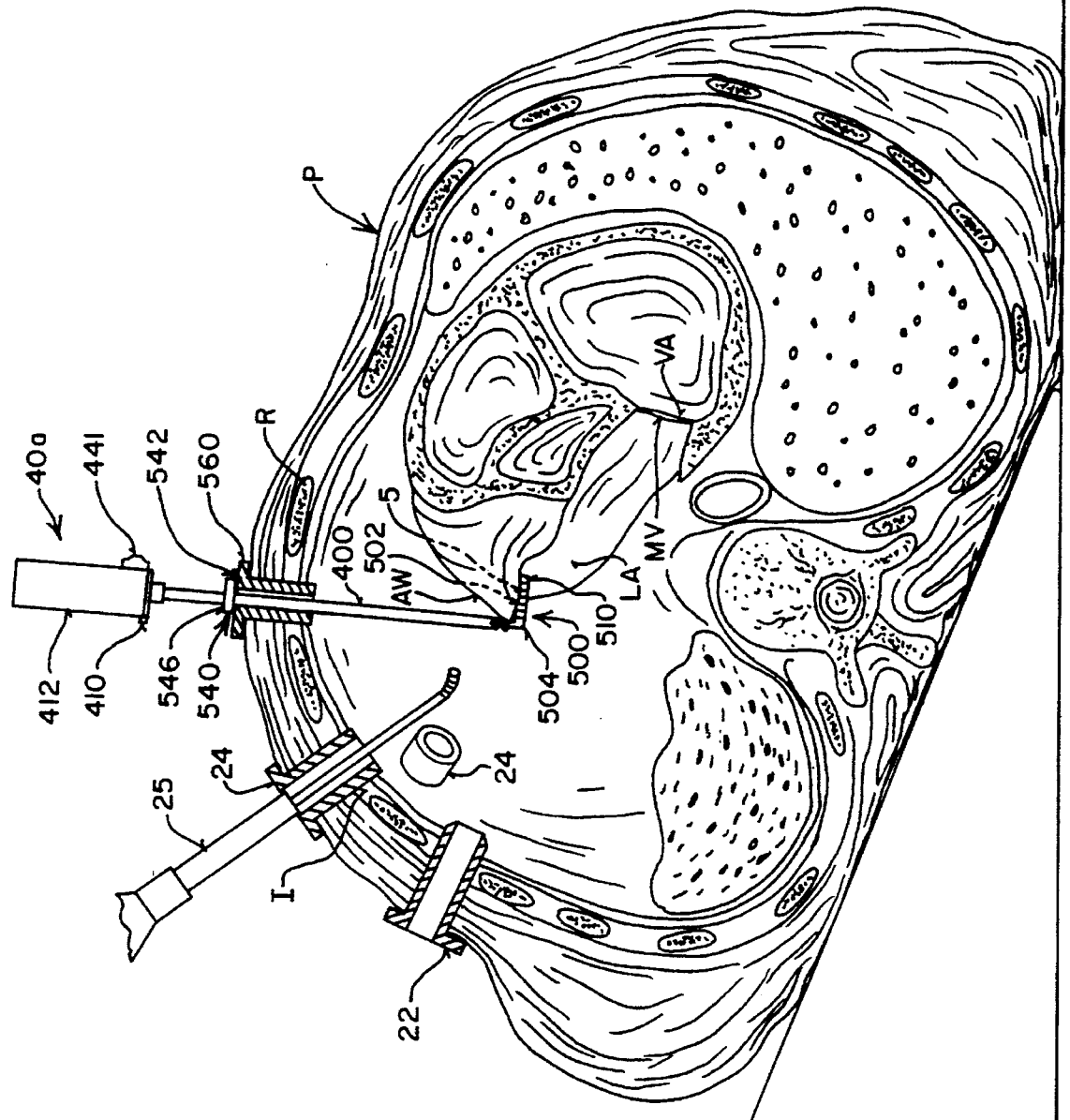

Referring to FIG. 31D, retractor 40a is now rotated so that tissue supporting member 500 is oriented with first lip 510 facing the atriotomy in the left atrium LA. The surgeon then manipulates handle 412 to position tissue supporting member 500 in the atriotomy so that the outer atrium wall AW is on contact surface 502. Once tissue supporting member 500 is in the desired position, the surgeon pulls retractor 40a proximally to retract atrium wall AW anteriorly, as shown in FIG. 31D. Atrium wall AW is prevented from sliding along or off of contact surface 502 by grooves 504 and first lip 510. Tissue supporting member 500 is wide enough to retract a substantial portion of atrium wall AW so that surgical instruments may be passed through the atriotomy for the mitral valve operation.

Tissue supporting member 500 extends deeply into the left atrium LA so that the interatrial septum S is effectively supported on contact surface 502. The interatrial septum S divides the left atrium LA from the right atrium (not shown), which is generally located anterior to the left atrium LA when the patient lies on his or her back. The interatrial septum S will therefore have a generally horizontal orientation and may tend to sag downward into the left atrium LA by gravity or other pressure differences between the left and right atria. Tissue supporting member 500 is well suited to support the interatrial septum S thereby preventing it from sagging into the left atrium LA. As discussed above, contact surface 502 preferably has a length between 25 and 40 mm and, if necessary, can be extended as far into the heart H as needed to retract interatrial septum S to expose the mitral valve.

To retain atrium wall AW in the retracted position, collar 540 is slid proximally against the outside surface of cannula 560. As discussed above, annular ring 546 has a diameter larger than the inner diameter of cannula 560 so that collar 540 will abut against the outside surface of cannula 560. Bolt 543 is then tightened to close annular ring 546 around shaft 400 so that shaft 400 will not move in the distal direction. Thus, the atrium wall AW will remain in the retracted position while leaving the surgeon's hands free. At this point, the mitral valve MV is exposed for an approach from the right lateral side of the chest via access cannula 22, as described in greater detail below.

As shown in FIG. 31D, tissue supporting member 500 is rotated after it has been connected to shaft 400 to face the left atrium LA. Alternatively, hook 552 of introducer 550 could engage third opening 523 in second lip 514 to hold tissue supporting member 500. In this configuration, tissue supporting member 500 would be introduced through access cannula 22 with first lip 510 distal of second lip 514 (rotated approximately 180 degrees from the configuration shown in FIGS. 31A–31C). Tissue supporting member 500 would then be connected to retractor 40a by engaging first opening 520 with hook 428 in the same manner described above.

After the mitral valve MV has been repaired or replaced, the above method is reversed to remove tissue supporting member 500 from the patient's thoracic cavity. The atrium wall AW is disengaged from contact surface 502 and tissue supporting member 500 is removed from the atriotomy and rotated into the position shown in FIG. 31B. Introducer 550 is reintroduced through access cannula 22 and connected to second opening 522 in tissue supporting member 500. Button 460 of retractor 40a is then pushed to release sleeve 438 so that shaft 400 returns to the releasable position. The surgeon then n-loves hook 428 out of first opening 520 and withdraws retractor 40a through cannula 560. Tissue supporting member 500 can then be withdrawn through access cannula 22 using introducer 550.

It will be understood that retractors 40 and 40a illustrated in FIGS. 1, 5, 15 and 26–31, respectively, are merely exemplary of the various means that may be used for retraction of left atrium LA. Another suitable means of retraction is described in published European patent application number PCT/US92/06186, the complete disclosure of which is incorporated herein by reference. That application describes a clip which may be applied to tissue by means of an introducer, and a flexible cable assembly attached to the clip which may be used to apply traction to the clip from outside of the patient's body. The clip may be applied to the wall of the left atrium LA on the anterior side of atriotomy 162 with the cable extending through a trocar sleeve 24, whereby atriotomy 162 is retracted open by applying traction to the cable. The cable may be attached to the patient's body, to the surgical drapes, or to another support structure outside of the body to maintain the atriotomy open during the procedure. Alternatively, one or more sutures (not shown) may be applied to the wall of left atrium LA anterior to atriotomy 162. The free ends of the sutures may be applied to an internal structure in the thoracic cavity, or withdrawn from the thoracic cavity through a puncture or a trocar sleeve 24 and attached to the patient's body or to the surgical drapes, thereby opening atriotomy 162. Other suitable means of retraction include devices having a collapsible and expandable frame (not pictured) which is insertable within atriotomy 162. When deployed, the frame urges the opposing sides of atriotomy 162 away from each other, and maintains the atriotomy open throughout the procedure until the device is removed.

With atriotomy 162 retracted open, the interior of heart H is accessible for the performance of an interventional procedure therein. Instruments may be introduced through access cannula 22 or trocar sleeves 24 and through atriotomy 162 to perform a procedure within left atrium LA. Additionally, such instruments may be extended through mitral valve MV into the left ventricle, or from the left ventricle through the aortic valve into the ascending aorta for inspection or intervention therein. In this way, the aortic valve may be repaired or replaced using techniques much like the mitral valve repair and replacement techniques described below.

When replacing mitral valve MV, it is often desirable to cut or remove all or a portion of the mitral valve leaflets VL. For this purpose, grasping forceps 112 may be used to grasp valve leaflet VL while angled scissors 110 and/or knife 134 are used to excise valve leaflet VL from the valve annulus VA. All or part of one or both valve leaflets VL may be cut or removed in this way. When removing valve leaflets VL, however, it is generally desirable to avoid permanently cutting or removing the chordae tendonae and papillary muscles (not shown) attached to the left ventricle. It has been found that a patient's chordae tendonae and papillary muscles may contribute to proper cardiac function even when a patient's natural valve has been replaced with a replacement valve.

At this point, it is usually necessary to size valve annulus VA so as to select a replacement valve 36 of the proper size for patient P. Various means may be used for sizing, but in one embodiment a sizing disk is introduced through access cannula 22, and the diameter of the sizing disk is compared to that of valve annulus VA. Preferred devices and methods for sizing valve annulus VA are described more fully below.

Various types of replacement valves are available for replacement of the mitral valve, and there are various ways of securing these replacement valves within the patient's heart. One common means of replacement valve attachment is suturing the prosthesis to the patient's natural valve annulus. Referring to FIG. 6, after valve leaflets VL have been removed, a plurality of sutures 198 are applied to valve annulus VA, under visualization by means of endoscope 25 (FIGS. 1–2) and/or by direct vision through passage 50 of access cannula 22. Each end of each suture 198 is attached to a curved needle 200. At least one and usually two needle drivers 202 are introduced into the thoracic cavity through trocar sleeves 24 and/or access cannula 22. A first of needle drivers 202 is used to drive a tip of needle 200 through valve annulus VA, while a second of needle drivers 202 is used to grasp the tip of needle 200 and pull it completely through valve annulus VA. After being applied to valve annulus VA, each suture 198 is withdrawn from the thoracic cavity through passage 50 of access cannula 22, and placed in one of slots 62 in organizing ring 30. Because a needle 200 is attached to both ends of each suture 198, each needle 200 may be driven through valve annulus VA in a single direction, then withdrawn from the thoracic cavity through passage 50 of access cannula 22. Preferably, each suture 198 is positioned within a slit 66 in retaining ring 64 (FIGS. 11A–11D) to frictionally engage the suture and keep it within slot 62.

Various types of stitches may be used in applying sutures 198 to valve annulus VA. In an exemplary embodiment, a "mattress" suture technique is used, wherein each needle 200 is driven through valve annulus VA from the ventricular side toward the atrial side of valve annulus VA. Alternatively, an "everting mattress" suture technique is used, wherein each needle 200 is driven through valve annulus VA from the atrial side toward the ventricular side of valve annulus VA. Various other types of stitches may also be used, depending upon the type of replacement valve to be utilized and the position in which it is to be mounted to valve annulus VA.

FIGS. 16A–16B illustrate the construction of needle drivers 202 in greater detail. Needle drivers 202 include a shaft 204 having a distal end 206 and a proximal end 208. An actuator 210 is attached to proximal end 208, and is constructed as described above in connection with FIG. 12A. Actuator 210 translates a push rod 212 extending through shaft 204. A stationary jaw 214 is fixed to distal end 206 of shaft 204, and a movable jaw 216 is pivotally mounted to stationary jaw 214. Movable jaw 216 is linked to push rod 212, whereby distal movement of push rod 212 closes movable jaw 216 against stationary jaw 214. Carbide surfaces as well as grooves or other textural features may be provided on the inner surfaces of jaws 214, 216 to enhance gripping of needles 200. Further, a locking mechanism (not shown) may be included on actuator 210 to lock jaws 214, 216 in the closed position.

Figure 7:
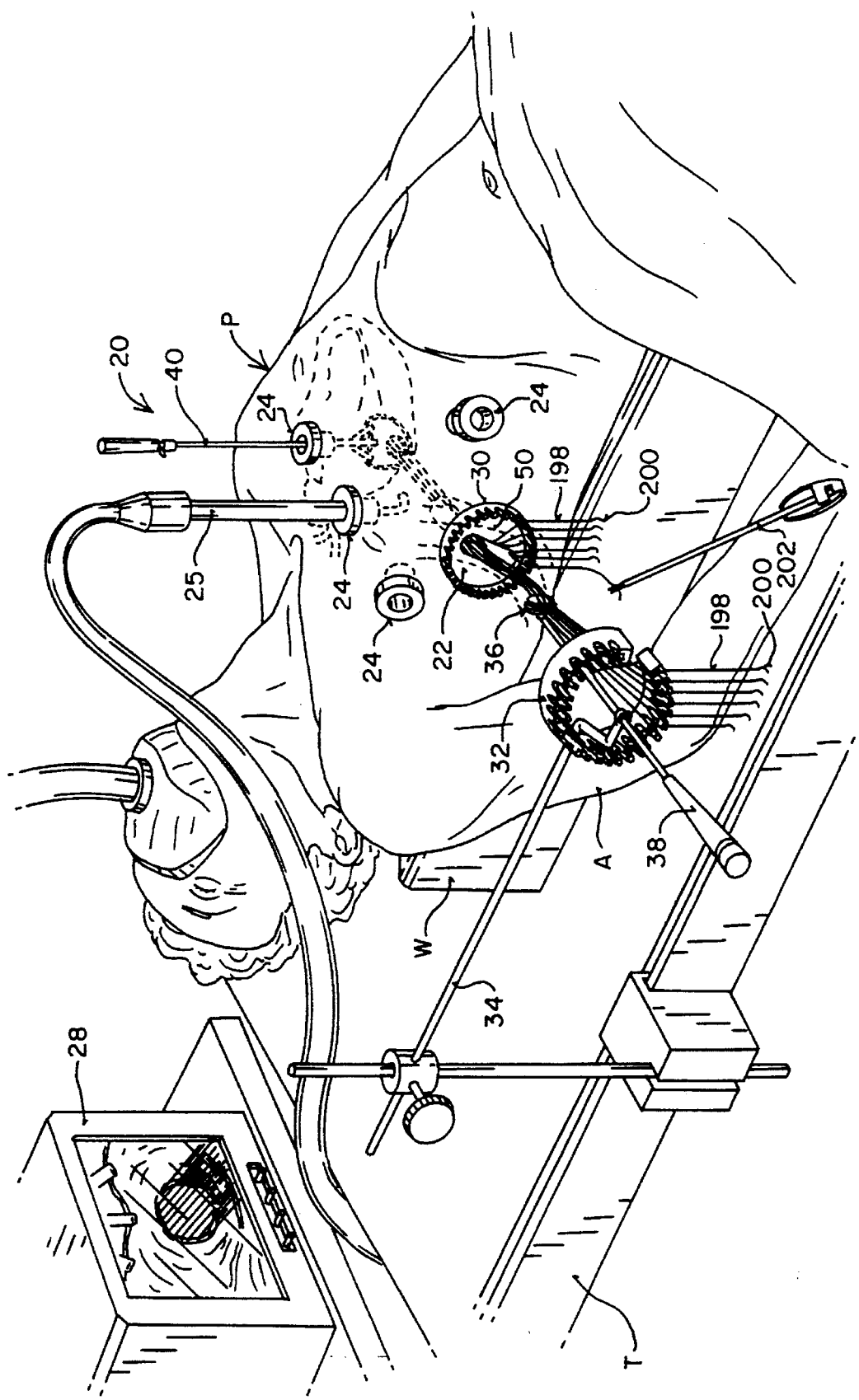
FIG. 7 is a perspective view of the system of FIG. 1 positioned in the patient, showing the application of sutures to a replacement valve.

Referring to FIG. 7, once all of sutures 198 have been withdrawn from the thoracic cavity and placed in slots 62 of organizing ring 30, the sutures are applied to replacement valve 36, held in position by introducer 38. Replacement valve 36 may be any of a variety of commercially available prostheses, including mechanical and bioprosthetic, stented and unstented, as described in Bodnar and Frater, *Replacement Cardiac Valves*, pp. 4–7, which has been incorporated herein by reference, and in Jamieson, "Modern Cardiac Valve Devices-Bioprostheses and Mechanical Prostheses: State of the Art," *J. Card. Surg.* 8:89–98 (1993). Mechanical valves may be of the caged ball type such as the Starr-Edwards valve (Baxter Healthcare Corp., Edwards CVS Div., Irvine, Calif.), the tilting disk type such as the Medtronic Hall valve (Medtronic, Inc., Minneapolis, Minn.), the Bjork-Shiley Monostrut valve (Shiley, Inc., Irvine, Calif.), the Omniscience® valve (Omniscience Medical Inc., Grove Heights, Minn.), as well as the bileaflet type such as the St. Jude Medical valve (St. Jude Medical, Inc., St. Paul, Minn.), the Baxter Duromedics valve (Baxter Healthcare Corp., Edwards CVS Div., Irvine, Calif.), the Carbomedics valve (Carbomedics, Inc., Austin, Tex.), or the Sorin valve (Sorin Biomedica, Saluggia, Italy). Bioprosthetic valves may be porcine aortic valves such as the Hancock II bioprosthesis (Medtronic, Inc., Minneapolis, Minn.), the Carpentier-Edwards supraannular bioprosthesis (Baxter Healthcare Corp., Edwards CVS Div., Irvine, Calif.), the Carpentier-Edwards stentless bioprosthesis (Baxter Healthcare Corp., Edwards CVS Div., Irvine, Calif.), the St. Jude-Bioimplant bioprosthesis (St. Jude Medical, Inc., St. Paul, Minn.), or the Medtronic Intact® bioprosthesis (Medtronic, Inc., Minneapolis, Minn.), as well as pericardial valves such as the Mitroflow bioprosthesis (Mitroflow International, Inc., Richmond, British Columbia, Canada), or the Carpentier-Edwards pericardial bioprostheses (Baxter Healthcare Corp., Edwards CVS Div., Irvine, Calif.). The invention also facilitates valve replacement with homografts and allografts, as well as with a variety of replacement valves not specifically listed here.

In an exemplary embodiment, the invention facilitates replacement of a patient's mitral valve with a mechanical bileaflet replacement valve such as the St. Jude Medical valve, illustrated in FIGS. 17A–17C. In this embodiment, replacement valve 36 comprises a ring-shaped frame 218 and a pair of leaflets 220 pivotally mounted to frame 218. In the open configuration illustrated in FIGS. 17A–17B, leaflets 220 are nearly parallel to each other, providing a flow passage 222 through which blood may flow in the direction of arrows 224. In the event of fluid pressure against the inner faces 226 of leaflets 220, leaflets 220 pivot into a closed configuration, blocking flow passage 222. A sewing ring 228 is attached to frame 218 to which sutures 198 may be applied for securing replacement valve 36 in the heart.

Figure 17A:
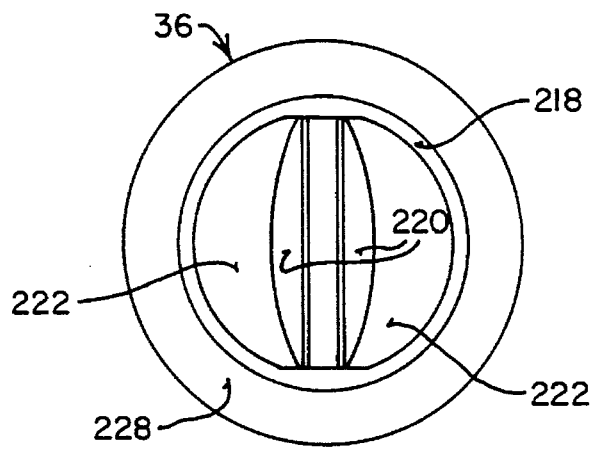
FIGS. 17A–17B are top and side views, respectively, of a replacement valve in the system of FIG. 1.
Figure 17C:
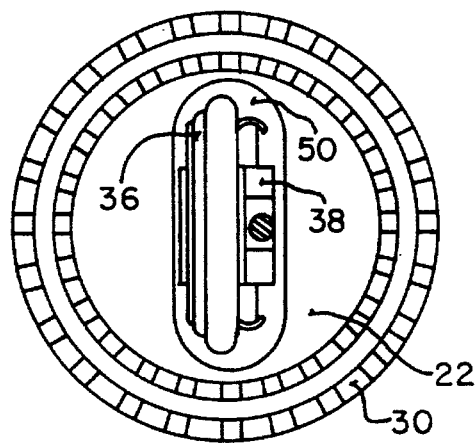
FIG. 17C is an end view of the replacement valve of FIGS. 17A–17B positioned in a passage of an access cannula in the system of FIG. 1.
Figure 17B:
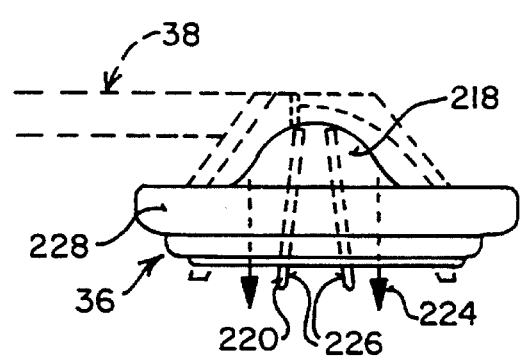

As illustrated in FIGS. 17B–17C, replacement valve 36 may be mounted to introducer 38 for introduction into the heart through passage 50 of access cannula 22. Replacement valve 36 may have various sizes according to the size of the mitral valve being replaced. However, the outer diameter of sewing ring 228 is usually about 19 mm to 35 mm, which, for most adult patients, is larger than the width of the third, fourth, fifth or sixth intercostal spaces, which range from 15 mm to 20 mm in width. The height of replacement valve 36, on the other hand, is smaller than the width of these intercostal spaces, usually being about 8 mm to 15 mm. Therefore, passage 50 is configured to allow replacement valve 36 to pass through it in an edge-first orientation, as illustrated in FIG. 17C.

Introducer 38 will now be described with reference to FIGS. 18–20. Introducer 38 includes a shaft 230 having a distal end 232, a proximal end 234, and an inner lumen 236 therebetween. Shaft 230 has a length selected to allow placement of replacement valve 36 in the mitral valve position within the patient's heart from outside of the patient's thoracic cavity, and is usually at least about 20 cm in length, and preferably about 25 cm to 35 cm in length. A handle 238 is attached to proximal end 234, and a rotatable knob 240 is mounted to handle 238 for pivoting the replacement valve 36 relative to shaft 230. A pull ring 242 extends proximally from pivot knob 240 for releasing replacement valve 36 from introducer 38. As best seen in FIGS. 20A–20B, push rod 244 extends through inner lumen 236, and is coupled at its distal end 248 to a pivot 250 which is pivotally mounted within a slot 252 at distal end 232 of shaft 230. A shank 254 extends distally from pivot 250 and has threads or other means for attachment to a valve holder 255 for replacement valve 36. Knob 240 is fixed to a threaded shaft 256 received within a threaded bore 258 in handle 238, whereby rotation of knob 240 translates threaded shaft 256 distally or proximally, depending upon the direction of rotation. Push rod 244 has a proximal end 260 which engages a distal end 262 of threaded shaft 256. A spring 264 biases push rod 244 in a proximal direction against distal end 262. In this way, rotation of knob 240 pulls or pushes push rod 244, thereby pivoting pivot 250 such that shank 254 extends either distally or laterally.

Referring to FIGS. 19A–19G, valve holder 255 includes a stationary arm 266 attached to shank 254, and a movable arm 268 pivotally mounted to stationary arm 266. Each of arms 266, 268 has an annular channel 270 configured to engage frame 218 of replacement valve 36 within flow channel 222 (FIG. 17A). Arms 266, 268 are further dimensioned and configured for introduction through passage 50 of access cannula 22 when replacement valve 36 is held in channels 270. As illustrated in FIG. 19A, when attached to shank 254 on introducer 38, valve holder 255 may be pivoted in the direction of arrow 272 by rotation of knob 240. In this way, the replacement valve 36 held by holder 255 may be introduced edge-first through passage 50 in access cannula 22, then pivoted approximately 90° to an orientation suitable for attachment in the mitral valve position within heart H.

To facilitate releasing replacement valve 36 from holder 55 from a location outside of the patient's body, a pull wire 274 is coupled to movable arm 268 by, for example, an anchor ball 276 disposed within an aperture 278 (see FIG. 20A). Pull wire 274 extends through an inner lumen (not shown) in push rod 244, and is attached at its proximal end 280 to pull ring 242. A spring 282 within an aperture 284 in knob 240 biases pull ring 242 in a distal direction. In this way, pulling on pull ring 242 pivots movable arm 268 as shown in FIG. 19C, allowing replacement valve 36 to be removed from channels 270. Anchor ball 276 and/or pull ring 242 may be configured so as to be removable from pull wire 244, allowing valve holder 255 to be removed from introducer 38 by decoupling arm 266 from shank 254.

In order to keep replacement valve 36 on holder 255 when holder 255 is not attached to introducer 38, a pair of holes 286 are provided in arm 266 in alignment with a corresponding pair of holes 288 in arm 268. When replacement valve 36 has been placed on holder 255, a suture (not shown)

may be tied through holes 286, 288 to prevent pivoting of arm 268, thereby retaining replacement valve 36 on holder 255. Once holder 255 has been attached to introducer 38, the suture may be removed, allowing arm 268 to pivot in response to rotation of knob 240.

It will frequently be desirable for valve holder 255 and replacement valve 36 to be pre-assembled, sterilized, and packaged together in a single sterile pack. In this way, upon opening the sterile pack in the operating room, the replacement valve 36 and holder 255 are ready for immediate surgical use. Further, it may be desirable for introducer 38 to be sterilized with replacement valve 36 and included in the same sterile pack. In such cases, holder 255 may be integrated with and non-removable from introducer 38, with replacement valve 36 being mounted to arms 266, 268 at the distal end of introducer 38 within the sterile pack. Alternatively, introducer 38 may be a reusable device which is attached to holder 255 and replacement valve 36 in the operating room at the time of the procedure.

As mentioned above, in order to select a replacement valve 36 which is of the appropriate size for patient P, valve annulus VA is usually sized prior to applying sutures 198 to valve annulus VA. Sizing may be accomplished in various ways, but in an exemplary embodiment, is performed by means of a sizing disk 290, illustrated in FIGS. 21–23, pivotally attached to introducer 38. Sizing disk 290 may be pivoted approximately 90° relative to shaft 230 of introducer 38, from an edge-first orientation suitable for introduction through access cannula 22, to a face-first orientation suitable for sizing valve annulus VA. As shown in FIGS. 22 and 23, sizing disk 290 is configured for attachment to shank 254 of introducer 38, preferably by means of a threaded hole 292. A notch 294 is provided in a proximal portion of disk 290 through which distal end 232 of shaft 230 may extend when disk 290 is in the edge-first orientation. An aperture 296 is disposed in the middle of disk 290 through which distal end 232 of shaft 230 may extend when disk 290 is in the face-first orientation. Preferably, a plurality of interchangeable sizing disks 290 of various diameters are provided for the procedure, allowing various sizing disks 290 to be introduced into heart H and compared with valve annulus VA until the diameter of the sizing disk corresponds to that of valve annulus VA.

In place of sizing disk 290, an expandable balloon or basket may be used for sizing valve annulus VA. Fluoroscopy, transesophageal echocardiography (TEE), epicardial or trans-thoracic ultra-sonography, or angiography may also be used to facilitate sizing valve annulus VA.

When the size of valve annulus VA has been identified, sizing disk 290 may be removed from introducer 38 and replaced by a replacement valve 36 of the appropriate size, mounted on holder 255. Introducer 38 may then be clamped to support stand 34 with replacement valve 36 positioned between first organizing ring 30 and second organizing ring 32, as illustrated in FIG. 7.

Sutures 198 are applied to replacement valve 36 by passing needles 200 through sewing ring 228 using needle drivers 202. Sutures 198 are then positioned in circumferentially spaced positions on second organizing ring 32. Second organizing ring 32 comprises, as illustrated in FIGS. 24A–24C, an inner ring 298 fixed to support stand 34, and an outer ring 300 rotatably mounted to inner ring 298. An elastomeric retaining ring 302 is disposed in an annular channel 304 in inner ring 298. Radial pins 303 are fixed to inner ring 298 and extend through slots 305 in outer ring 300, thereby limiting the rotation of outer ring 300 relative to inner ring 298. A plurality of slots 306 are disposed in circumferentially spaced positions about inner ring 298, and a corresponding number of slots 308 alignable with slots 306 are disposed in outer ring 300. Retaining ring 302 has a plurality of slits 310 which are aligned with slots 306 in inner ring 298. A clamp 312 for clamping shaft 230 of introducer 38 is disposed on an extension 314 fixed to support stand 34.

After being applied to replacement valve 36, sutures 198 may be positioned within inner slots 306, slits 310, and outer slots 308. Once all of sutures 298 have been applied to replacement valve 36 and positioned in organizing ring 32, outer ring 300 may be rotated relative to inner ring 298, thereby locking sutures 298 in position.

Figure 8A:
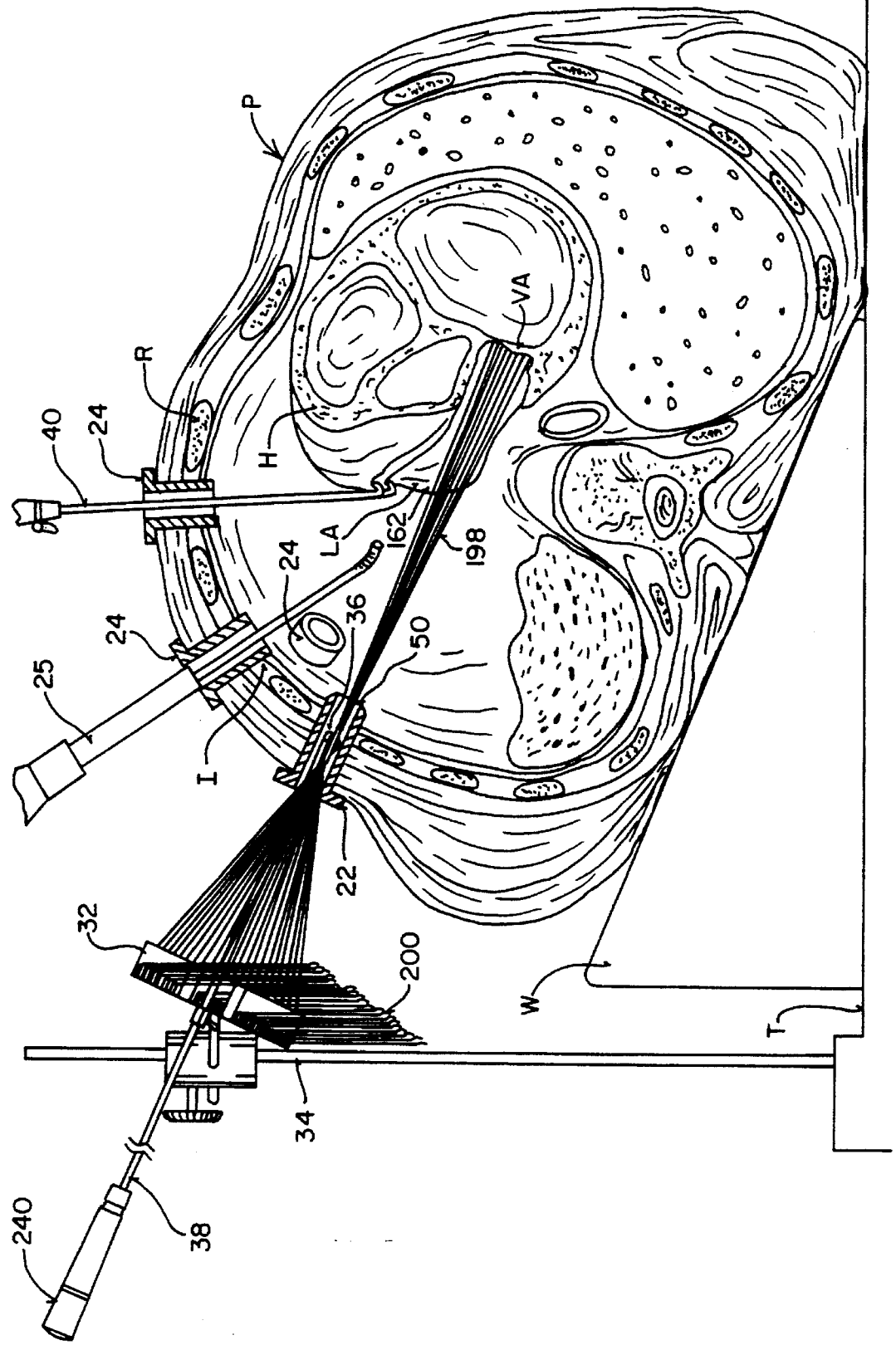
FIGS. 8A–8B are transverse cross-sectional views of the system and patient of FIG. 1 taken through the patient's thorax, showing the introduction of the replacement valve into the left atrium and the tying of knots in the sutures to secure the prosthesis in the patient's heart.

Referring now to FIG. 8A, replacement valve 36 may then be introduced into the left atrium LA by advancing introducer 38 through passage 50 of access cannula 22. Replacement valve 36 is oriented on introducer 38 so as to be introduced edge-first through passage 50. As replacement valve 36 is advanced into the thoracic cavity, organizing ring 32 maintains tension on sutures 198, allowing replacement valve 36 to slide along sutures 198. Introducer 38 is advanced through atriotomy 162 so that replacement valve 36 is disposed within left atrium LA. Replacement valve 36 is then pivoted on introducer 38 by rotating knob 240, so that sewing ring 228 of replacement valve 36 (FIG. 17A) may be aligned with valve annulus VA.

Figure 8B:
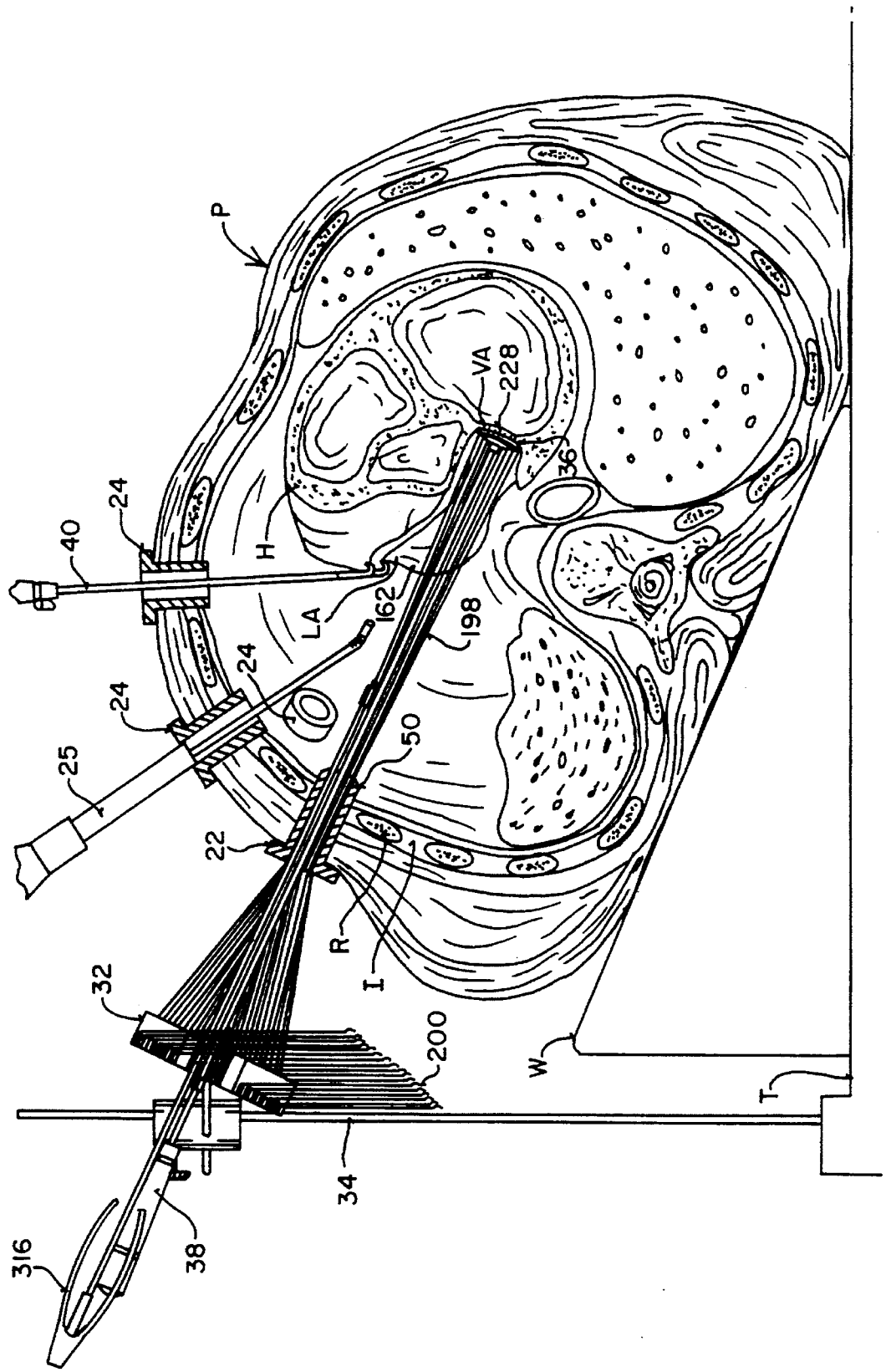

Introducer 38 is then advanced further into left atrium LA so as to position replacement valve 36 against or within valve annulus VA, as illustrated in FIG. 8B. Square or overhand knots are then formed in sutures 198 outside of the patient's thoracic cavity, and the knots are pushed by a knot pusher 316 through passage 50 and atriotomy 162 toward sewing ring 228 of replacement valve 36.

While knot pusher 316 may have a variety of configurations, an exemplary embodiment is illustrated in FIGS. 25A–25B. Knot pusher 316 comprises a shaft 318 having a distal end 320 and a proximal end 322, to which is connected an actuator 324 constructed like actuator 120 described above in connection with FIG. 12A. Actuator 324 translates a push rod 326 extending through shaft 318. A pair of movable jaws 328 are pivotally mounted to distal end 320 of shaft 318, and are coupled to push rod 326 such that proximal movement of push rod 326 opens jaws 328. A notch 330 at the distal end of each jaw 328 is configured to receive a suture 198.

In use, a first free end of a suture 198 is tied in a loop or slip knot over a second free end of suture 198, and jaws 328 are positioned just proximal to the knot. Jaws 328 are then opened such that each free end of suture 198 is positioned within a notch 330 at the distal end of jaws 328 and the slip knot is disposed centrally between jaws 328. While holding tension on the free ends of the sutures outside the thoracic cavity, knot pusher 316 is advanced distally, pushing the slip knot through passage 50 of access cannula 22 and atriotomy 162 until the slip knot engages sewing ring 228 of replacement valve 36.

Figure 9:
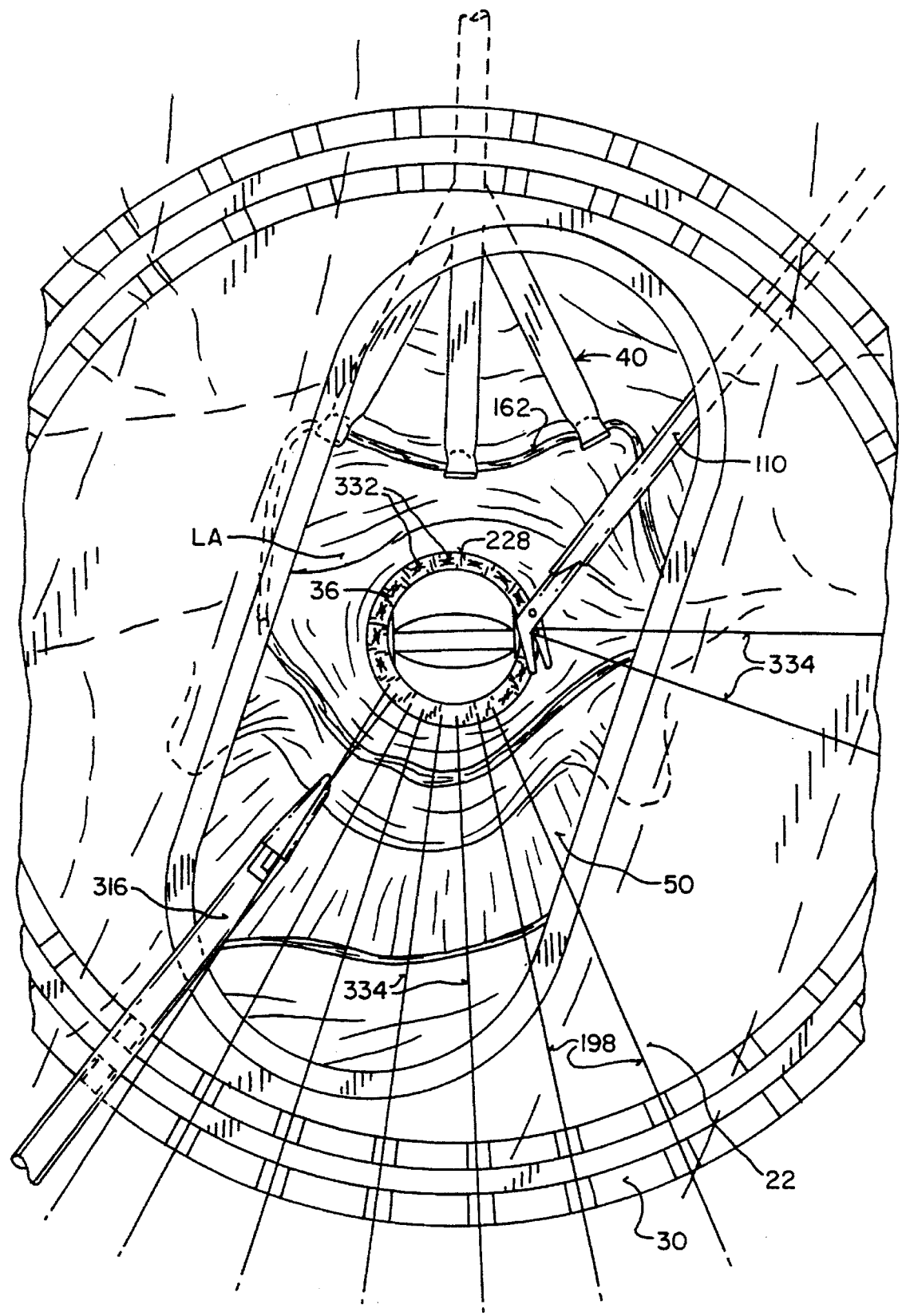
FIG. 9 is a top view looking into the patient's thoracic cavity through a passage of an access cannula in the system of FIG. 1, showing pushing the knots toward the replacement valve and trimming the free ends of the sutures.
Figure 10:
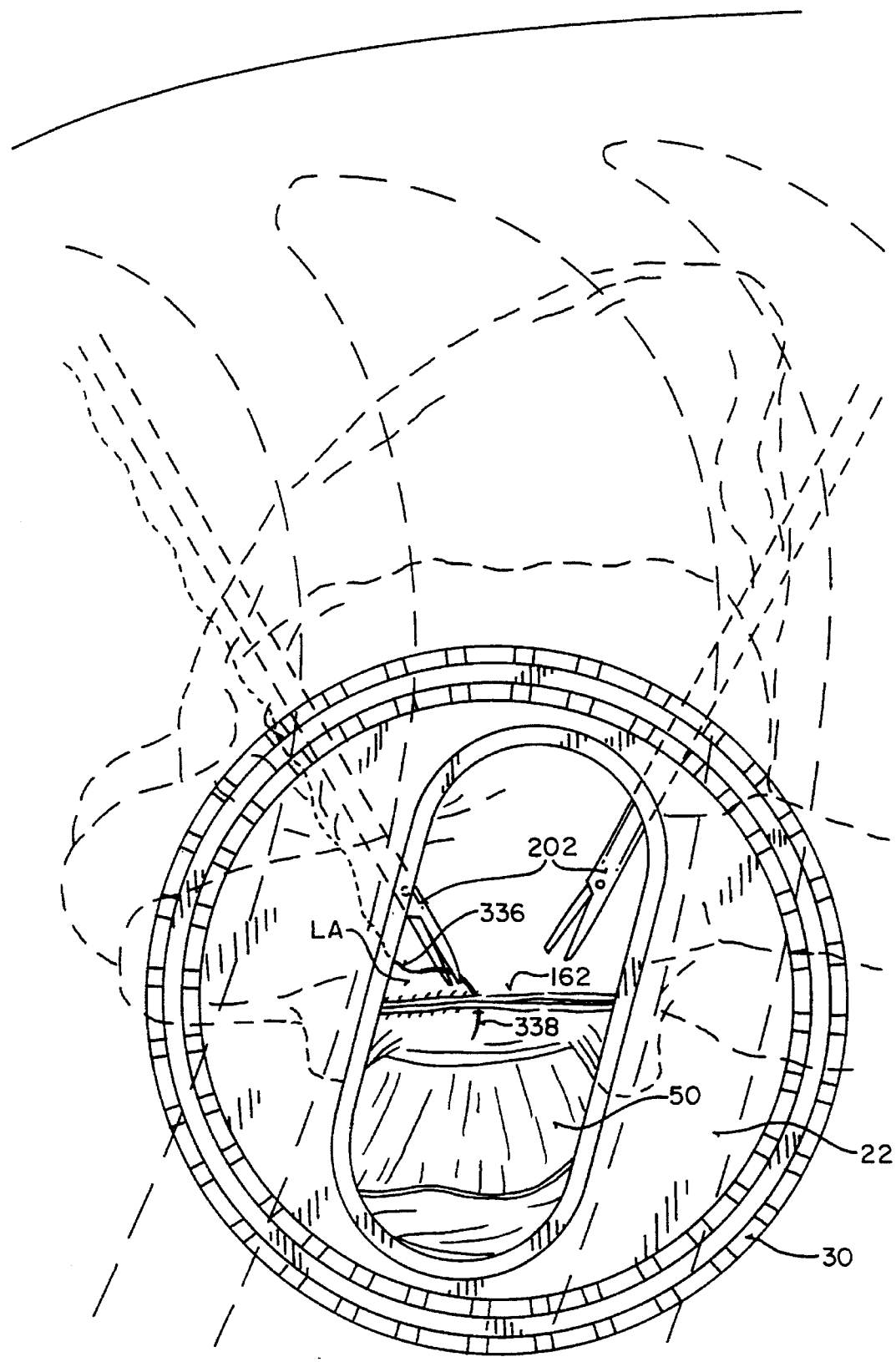
FIG. 10 is a top view looking into the patient's thoracic cavity through a passage of an access cannula in the system of FIG. 1, showing the closure of the patient's left atrium.

Referring now to FIG. 9, when a plurality of knots 332 (usually 5 to 8) have been tied and pushed against sewing ring 228 by knot pusher 316, knots 332 are cinched down tightly, and free ends 334 are trimmed using scissors 110 or other cutting device.

It will be understood to those of ordinary skill in the art that the thoracoscopic devices and methods disclosed above for tissue manipulation, retraction, cutting, suturing, and the like may be used to accomplish procedures such as annuloplasty, commissurotomy, quadrangular resection, shortening and reattachment of chordae tendonae, and various other valve repair procedures. To perform annuloplasty, valve annulus VA is contracted by suturing a portion of the valve annulus so as to overlap an adjacent portion, or by attaching a prosthetic annuloplasty device such as a Carpentier or Duran annuloplasty ring (not shown) to valve annulus VA to reduce its diameter. To perform commissurotomy, the valve leaflets VL are separated by cutting between them where they have fused together due to calcification or disease. To perform quandrangular resection, valve leaflets VL are shortened or narrowed by excising a portion of one or more leaflets VL, and reattaching the remaining portions of the leaflet by suturing. The chordae tendonae (not shown), which act as resilient springs between valve leaflets VL and the papillary muscles (not shown) attached to the heart wall in the left ventricle LV, may be shortened by excising a portion thereof and reattaching the ends of the remaining portions by suturing. Similarly, severed chordae tendonae may be restored by reattachment of the severed ends with sutures. Open-chest techniques for performing such procedures are described in detail in Kirklin and Barratt-Boyes, *Cardiac Surgery*, pp. 329–340, the disclosure of which has been incorporated herein by reference.

When the valve replacement or other surgical procedure in left atrium LA is completed, atriotomy 162 is closed. Sutures, thoracoscopic staples or other types of closure devices may be used for this purpose. In one embodiment, illustrated in FIG. 10, atriotomy 162 is closed by suturing, wherein needle drivers 202 are introduced through trocar sleeves 24 and/or access cannula 22, and a suture 336 having a needle 338 attached to an end thereof is used to sew up atriotomy 162 using conventional suturing techniques. Before and/or during closure, a suction/irrigation tube (not shown) is usually introduced through a trocar sleeve 24 and into left atrium LA or left ventricle LV to remove any air therein and to fill the heart chambers with a saline solution.

After atriotomy 162 has been closed, any remaining instruments are removed from the thoracic cavity. A chest tube may be introduced through one of trocar sleeves 24 to facilitate evacuation of the pleural cavity. Access cannula 22 and trocar sleeves 24 are then removed from the chest wall, and the incisions or penetrations through which they were introduced are closed, usually by suturing or stapling.

The patient's lung may then be reinflated, and cardiac function may be restarted. As described in co-pending application Ser. No. 07/991,188, which has been incorporated herein by reference, infusion of cardioplegic fluid through aortic occlusion catheter 82 and/or retroperfusion catheter 102 is discontinued, and a saline solution is infused through one or both of these catheters to irrigate the heart and coronary arteries (see FIG. 3). The saline solution, along with blood, other fluids, air, thrombus, and other emboli within the heart or coronary arteries are then aspirated through the inner lumen of aortic occlusion catheter 82, as well as through venous cannula 70 and/or pulmonary venting catheter 79. Occlusion balloon 88 on aortic occlusion catheter 82 is then deflated, allowing warm, oxygenated blood to flow into the coronary arteries to perfuse the myocardium. Cardiac contractions will usually begin soon thereafter. In some cases, electrical defibrillation may be necessary to help restore cardiac function. Aortic occlusion catheter 82 and retroperfusion catheter 102 may then be removed from the patient. Cardiopulmonary bypass is then discontinued, and arterial cannula 78, venous cannula 70, and pulmonary venting catheter 79 are removed from the patient.

In addition to performing mitral valve repair and replacement, the techniques of the invention also facilitate surgical intervention into other regions of the heart and great vessels. The devices and methods described above may be used to form an opening directly into the left ventricle, right atrium, or right ventricle, or into a great vessel such as the aorta, superior vena cava, inferior vena cava, pulmonary artery, or pulmonary vein, for surgical intervention in such cavities. For example, a penetration may be made in the wall of the aorta, and the aortic valve may be repaired or replaced with a prosthesis, using techniques and devices like those described above for mitral valve replacement. Moreover, the devices and methods of the invention also facilitate intercardiac procedures such as repair of atrial or ventricular septal defects, electrophysiological mapping and ablation of the myocardium, myocardial drilling, and other procedures. Furthermore, devices may be introduced through an opening into the heart or great vessel and advanced therefrom into vessels such as the coronary arteries to perform procedures such as angioplasty, atherectomy, coronary artery bypass grafting, or treatment of aneurysms.

While the above is a complete description of the preferred embodiments of the invention, various alternatives, modifications and equivalents may be used. Therefore, the above description should not be taken as limiting the scope of the invention, which is defined by the appended claims.

What is claimed is:

1. A method of retracting an incised opening in a wall of a chamber in a patient's heart, the method comprising the steps of:

introducing a tissue supporting member, releasably connected directly to an introducer, into the patient's thoracic cavity through a first percutaneous intercostal penetration, within a first intercostal space between two adjacent ribs, the tissue supporting member having a contact surface with a first length and a first width;

introducing a shaft having a longitudinal axis through a second percutaneous intercostal penetration, within a second intercostal space between two adjacent ribs, the shaft having a diameter smaller than the first width and the first length;

coupling the tissue supporting member to the shaft within the patient's thoracic cavity while holding the tissue supporting member with the introducer;

positioning the tissue supporting member within an incised opening in a chamber wall of the patient's heart;

manipulating said shaft from outside the patient's chest to position the contact surface of the tissue support member into supportive contact with the chamber wall; and applying a force to the shaft to retract the chamber wall thereby enlarging the opening.

2. The method of claim 1 wherein the tissue supporting member introducing step is carried out with the first percutaneous intercostal penetration being created in a right lateral side of the patient's chest.

3. The method of claim 1 wherein the shaft introducing step is carried out with the second percutaneous intercostal penetration being created in an anterior portion of the patient's chest.

4. The method of claim 1 wherein the applying step is carried out with the chamber wall being retracted anteriorly.

5. The method of claim 1 wherein the tissue supporting member introducing step is carried out with the tissue supporting member being introduced through a cannula positioned in the first percutaneous intercostal penetration.

6. The method of claim 1 further comprising the step of viewing the patient's heart through a scope extending through a third percutaneous intercostal penetration in the patient's chest.

7. The method of claim 1 further comprising the step of:
introducing an instrument through the first percutaneous intercostal penetration and through the opening; and
performing a procedure on the patient's heart with the instrument.

8. The method of claim 7 wherein the performing step is a valve replacement.

9. The method of claim 8 wherein the performing step is a mitral valve replacement.

10. The method of claim 7 wherein the opening is in a left atrium of the patient's heart.

11. The method of claim 10 wherein the tissue supporting member introducing step is carried out with the supporting member having said first length of sufficient length to extend into the left atrium to engage the interatrial septum.

12. The method of claim 1 wherein the tissue supporting member introducing step is carried out with the tissue supporting member being introduced through the first percutaneous penetration by a second shaft, the second shaft having means at a distal end for releasably holding the tissue supporting member.

13. The method of claim 12 further comprising the step of: releasing the tissue supporting member from the second shaft after connecting the tissue supporting member to the first shaft.

14. The method of claim 1 further including the step of, before the tissue supporting member introducing step, arresting the heart.

15. The method of claim 14 further including the step of, before the arresting step, establishing cardiopulmonary bypass.

16. The method of claim 1 wherein said contact surface of said tissue support member generally extends in a direction away from the longitudinal axis of said shaft.

17. The method of claim 16 wherein said coupling step is accomplished by connecting said shaft to one end of said tissue support member.

18. The method of claim 17 wherein said positioning step includes the step of inserting an opposite second end of said tissue support member into the incised opening of the left atrium until a first lip portion thereof, extending rearwardly from said contact surface, supportably engages the interatrial septum.

19. The method of claim 18 wherein the contact surface of the tissue support member extends continuously between said first end and said second end.

20. The method of claim 19 wherein the contact surface has a curvature selected to conform to the inner surface of the incised opening.

21. The method of claim 1 wherein the tissue support member introducing step and the shaft introducing step are performed at generally right angles relative one another.

* * * * *